United States Patent
Breitbart et al.

(10) Patent No.: US 9,403,887 B2
(45) Date of Patent: Aug. 2, 2016

(54) ENDOTHELIAL CELL-SPECIFIC POLYNUCLEOTIDES AND USE THEREOF

(71) Applicant: Vascular Biogenics Ltd., Or Yehuda (IL)

(72) Inventors: Eyal Breitbart, Hasmonaim (IL); Livnat Bangio, Petach-Tikva (IL); Reshef Tal, Or Yehuda (IL)

(73) Assignee: Vascular Biogenics Ltd., Or Yehuda (IL)

( * ) Notice: Subject to any disclaimer, the term of this patent is extended or adjusted under 35 U.S.C. 154(b) by 0 days.

(21) Appl. No.: 14/495,614

(22) Filed: Sep. 24, 2014

(65) Prior Publication Data

US 2015/0111957 A1    Apr. 23, 2015

Related U.S. Application Data

(62) Division of application No. 13/163,776, filed on Jun. 20, 2011, now abandoned, which is a division of application No. 12/309,856, filed as application No. PCT/IL2007/000959 on Jul. 31, 2007, now abandoned.

(60) Provisional application No. 60/834,157, filed on Jul. 31, 2006.

(51) Int. Cl.

| | | |
|---|---|---|
| *C07H 21/04* | (2006.01) |
| *C12N 15/113* | (2010.01) |
| *C12N 15/12* | (2006.01) |
| *C12N 15/85* | (2006.01) |
| *C12N 15/861* | (2006.01) |
| *C07K 14/47* | (2006.01) |
| *A61K 48/00* | (2006.01) |
| *C12N 7/00* | (2006.01) |
| *C12N 15/86* | (2006.01) |

(52) U.S. Cl.
CPC ........... *C07K 14/4705* (2013.01); *A61K 48/005* (2013.01); *A61K 48/0058* (2013.01); *C07K 14/4702* (2013.01); *C12N 7/00* (2013.01); *C12N 15/86* (2013.01); *C12N 2710/10343* (2013.01); *C12N 2710/10371* (2013.01); *C12N 2799/022* (2013.01); *C12N 2799/04* (2013.01); *C12N 2830/002* (2013.01); *C12N 2830/008* (2013.01)

(58) Field of Classification Search
CPC ........ C12N 15/11; C12N 15/85; C12N 15/86; C12N 15/79; C12N 15/861; C12N 2830/008; C07K 14/57536; C07K 14/4705
USPC ...................... 536/24.1; 435/320.1; 424/199.1
See application file for complete search history.

(56) References Cited

U.S. PATENT DOCUMENTS

| | | | |
|---|---|---|---|
| 7,067,649 | B2 | 6/2006 | Harats |
| 7,579,327 | B2 | 8/2009 | Harats et al. |
| 2004/0048280 | A1 | 3/2004 | Harats |
| 2005/0202450 | A1 | 9/2005 | Huang et al. |
| 2009/0326052 | A1 | 12/2009 | Harats et al. |
| 2010/0298226 | A1 | 11/2010 | Breitbart et al. |
| 2011/0201677 | A1 | 8/2011 | Harats et al. |
| 2011/0319479 | A1 | 12/2011 | Breitbart et al. |
| 2012/0201790 | A1 | 8/2012 | Harats et al. |
| 2013/0052165 | A1 | 2/2013 | Bangio et al. |
| 2013/0209450 | A1 | 8/2013 | Cohen et al. |
| 2013/0280216 | A1 | 10/2013 | Cohen et al. |
| 2013/0280217 | A1 | 10/2013 | Cohen et al. |
| 2013/0295053 | A1 | 11/2013 | Bangio et al. |
| 2013/0296404 | A1 | 11/2013 | Harats et al. |
| 2013/0303595 | A1 | 11/2013 | Cohen et al. |
| 2014/0010785 | A1 | 1/2014 | Cohen et al. |

FOREIGN PATENT DOCUMENTS

| | | | |
|---|---|---|---|
| WO | WO-0010578 A1 | | 3/2000 |
| WO | WO 02/40629 | * | 5/2002 |
| WO | WO-0240629 A2 | | 5/2002 |
| WO | WO-03093409 A2 | | 11/2003 |
| WO | WO-2008015675 A2 | | 2/2008 |
| WO | WO-2011083464 A2 | | 7/2011 |
| WO | WO-2011083466 A1 | | 7/2011 |
| WO | WO-2011086509 A1 | | 7/2011 |
| WO | WO-2012052878-AI | | 4/2012 |

OTHER PUBLICATIONS

Medina et al. (2004) Hepatology, vol. 39(5), 1185-1195.*
Hooper et al. (2003) Clin. Exp. Ophthal., vol. 31, 376-391.*
Ohno-Matsui et al. (2002), Am. J. Path., vol. 160(2), 711-719.*
Baek, J,H., et al., "OS-9 interacts with hypoxia-inducible factor 1alpha and prolyl hydroxylases to promote oxygen-dependent degradation of HIF-1alpha," Molecular Cell 17(4):503-512, Cell Press, United States (2005).
Clark, "Missense Mutations May Have Major or Minor Effects;" Molecular Biology 13:337 (2005).
Communication Pursuant to Article 94(3) EPC for EP Application No. 07790014.0, Munich, Germany, mailed on Apr. 11, 2011.
Dery, M.A., et al., "Hypoxia-inducible factor 1: regulation by hypoxic and non-hypoxic activators," The International Journal of Biochemistry & Cell Biology 37(3):535-540, Elsevier, Netherlands (2005).
Fu, R-B., et al., "Construction of eukaryotic expression vectors of two mutants of hypoxia-inducible factor-1 and their expressions in human microvascular endothelial cells," accessed at MEDLINE database [Online], database accession No. NLM16305953, accessed on Feb. 2, 2010, 1 page (2005).

(Continued)

*Primary Examiner* — Anne Marie S Wehbe
(74) *Attorney, Agent, or Firm* — Sterne, Kessler, Goldstein & Fox P.L.L.C.

(57) ABSTRACT

An isolated polynucleotide is disclosed comprising a nucleic acid sequence encoding a polypeptide having an amino acid sequence of HIF-1alpha, the polypeptide being stably expressed and constitutively active. Isolated polypeptides encoded by same are also disclosed and uses thereof.

23 Claims, 19 Drawing Sheets

(56) References Cited

OTHER PUBLICATIONS

Fu, R-B., et al., "Construction of eukaryotic expression vectors of two mutants of hypoxia-inducible factor-1 and their expressions in human microvascular endothelial cells," Academic Journal of the First Medical College of PLA 25(11):1348-1351, Guangzhou Shi Tonghe Zhen : Di 1 jun yi da xue, China (2005).
Genevaux, P., et al., "Scanning mutagenesis identifies amino acid residues essential for the in vivo activity of the *Escherichia coli* DnaJ (Hsp40) J-domain," Genetics 162(3):1045-1053, Genetics Society of America, United States (2002).
Graven, K.K., et al., "HIF-2α regulates glyceraldehyde-3-phosphate dehydrogenase expression in endothelial cells," Biochimica et biophysica acta 1626(1-3):10-18, Elsevier, Netherlands (2003).
Harats, D., et al., "Targeting Gene Expression to the Vascular Wall in Transgenic Mice," GenBank U07982.1, 2 pages (1995).
Hooper, C.Y. and Guymer, R.H., "New treatments in age-related macular degeneration," Clinical & Experimental Ophthalmology 31(5):376-391, Wiley-Blackwell, Australia (2003).
International Preliminary Report on Patentability for International Application No. PCT/IL2007/000959, The International Bureau of WIPO, Switzerland, mailed Feb. 12, 2009.
International Preliminary Examination Report for International Application No. PCT/IL01/01059, IPEA/US, United States, mailed on Jan. 28, 2005.
International Preliminary Examination Report for International Application No. PCT/IL03/00347, IPEA/US, United States, mailed on May 26, 2005.
International Search Report for International Application No. PCT/IL2007/000959, ISA/US, United States, mailed on Sep. 29, 2008.
International Search Report for International Application No. PCT/IL01/01059, ISA/US, United States, mailed on May 4, 2004.
International Search Report for International Application No. PCT/IL03/00347, ISA/US, United States, mailed on Jan. 28, 2005.
Office Action mailed Apr. 26, 2013, in U.S. Appl. No. 13/454,171, Dror, H., et al., filed Apr. 24, 2012.
Office Action mailed Dec. 27, 2013, in U.S. Appl. No. 13/800,478, Dror, H., et al., filed Mar. 13, 2013.
Office Action mailed Dec. 7, 2011, in U.S. Appl. No. 13/094,900, Dror, H., et al., filed Apr. 27, 2011.
Office Action mailed Jun. 13, 2013, in U.S. Appl. No. 12/457,200, Dror, H., et al., filed Jun. 3, 2009.
Office Action mailed Jun. 17, 2013, in U.S. Appl. No. 13/094,900, Dror, H., et al., filed Apr. 27, 2011.
Office Action mailed Nov. 23, 2012, in U.S. Appl. No. 13/454,171, Dror, H., et al., filed Apr. 24, 2012.
Office Action mailed on Apr. 6, 2007, in U.S. Appl. No. 10/975,619, Dror, H., et al., filed Oct. 29, 2004.
Office Action mailed on Apr. 10, 2008, in U.S. Appl. No. 10/975,619, Dror, H., et al., filed Oct. 29, 2004.
Office Action mailed on Jan. 22, 2010, in U.S. Appl. No. 12/457,200, Dror, H., et al., filed Jun. 3, 2009.
Office Action mailed on Jul. 14, 2004, in U.S. Appl. No. 10/135,447, Dror, H., et al., filed May 1, 2002.
Office Action mailed on Jun. 4, 2010, in U.S. Appl. No. 12/457,200, Dror, H., et al., filed Jun. 3, 2009.
Office Action mailed on Nov. 10, 2010, in U.S. Appl. No. 12/457,200, Dror, H., et al., filed Jun. 3, 2009.
Office Action mailed on Nov. 18, 2013, in U.S. Appl. No. 12/457,200, Dror, H., et al., filed Jun. 3, 2009.
Office Action mailed Sep. 9, 2013, in U.S. Appl. No. 13/454,171, Dror, H., et al., filed Apr. 24, 2012.
Official Action mailed Dec. 21, 2010 in U.S. Appl. No. 12/309,856, Eyal B., et al., filed Feb. 2, 2009.
Official Action mailed Oct. 4, 2010 in U.S. Appl. No. 12/309,856, Eyal B., et al., filed Feb. 2, 2009.
Ohno-Matsui, K., et al., "Inducible Expression of Vascular Endothelial Growth Factor in Adult Mice Causes Severe Proliferative Retinopathy and Retinal Detachment," The American Journal of Pathology 160(2):711-719, American Assn. of Pathologists, United States (2002).
Rebar, E.J., "Development of pro-angiogenic engineered transcription factors for the treatment of cardiovascular disease," Expert Opinion on Investigational Drugs 13(7):829-839, Informa Healthcare, England, (2004).
Shyu, K-G., et al., "Intramyocardial injection of naked DNA encoding HIF-1α/VP16 hybrid to enhance angiogenesis in an acute myocardial infarction model in the rat," Cardiovascular Research 54(3):576-583, Oxford Journals, England (2002).
Supplementary European Search Report and the European Search Opinon for European Patent Application No. EP 07 79 0014, Munich, Germany, mailed on May 7, 2010.
Tal, R., et al., "Activation of C-transactivation domain is essential for optimal HIF-1α-mediated transcriptional and angiogneic effects," Microvascular Research 76(1):1-6, Elsevier, United States (2008).
Wang, G.L., et al., "Hypoxia-inducible factor 1 is a basic-helix-loop-helix-PAS heterodimer regulated by cellular $O_2$ tension," Proceedings of the National Academy of Sciences USA 92(12):5510-5514, National Academy of Sciences, United States (1995).
Written Opinion for International Application No. PCT/IL07/00959, ISA/US, United States, mailed on Sep. 29, 2008.
Written Opinion of the International Search Authority for International Application No. PCT/IL01/01059, IPEA/US, United States, mailed on Nov. 2, 2004.
Yamashita, K., et al., "Molecular Regulation of the Endothelin-1 Gene by Hypoxia: Contributions of Hypoxia-Inducible Factor-1, Activator Protein-1, GATA-2, and p300/CBP," The Journal of Biological Chemistry 276(16):12645-12653, American Society for Biochemistry and Molecular Biology, United States (2001).
Papadakis, E.D., et al., "Promoters and Control Elements: Designing Expression Cassettes for Gene Therapy," *Current Gene Therapy* *4(1)*:89-113, Bentham Science Publishers, Netherlands (Mar. 2004).

\* cited by examiner

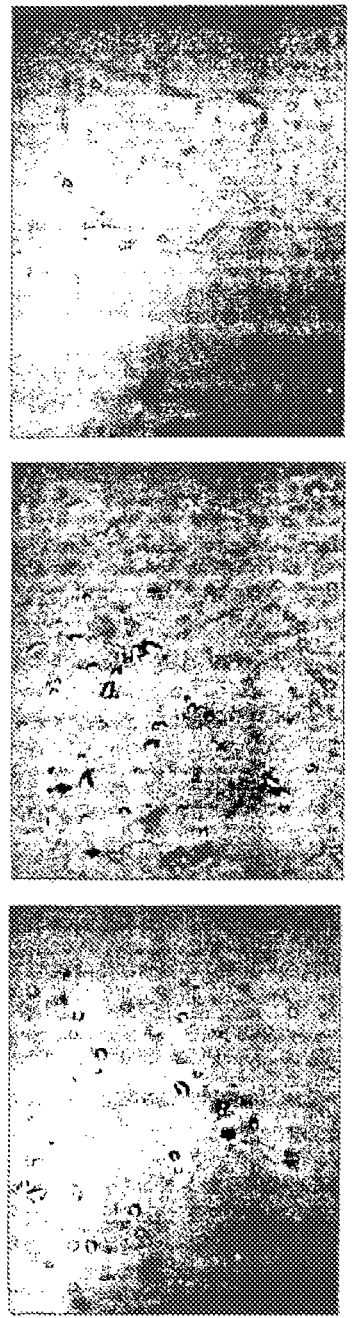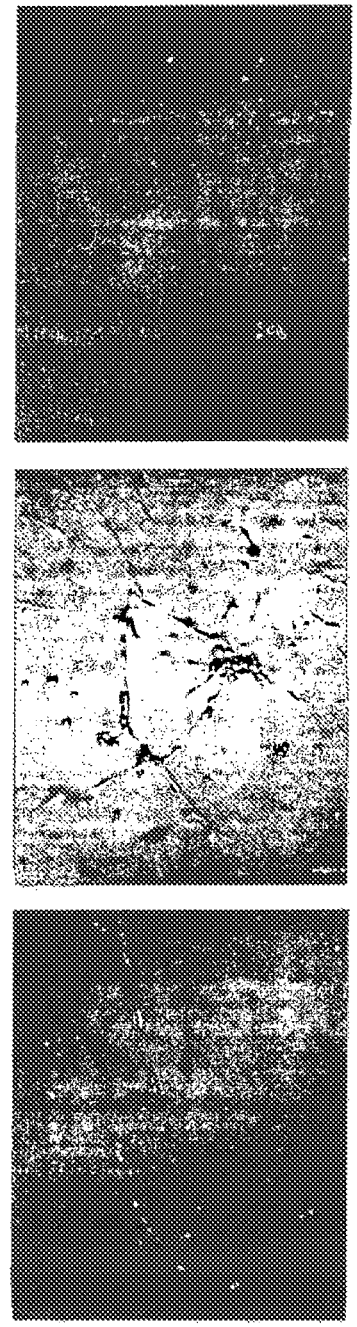

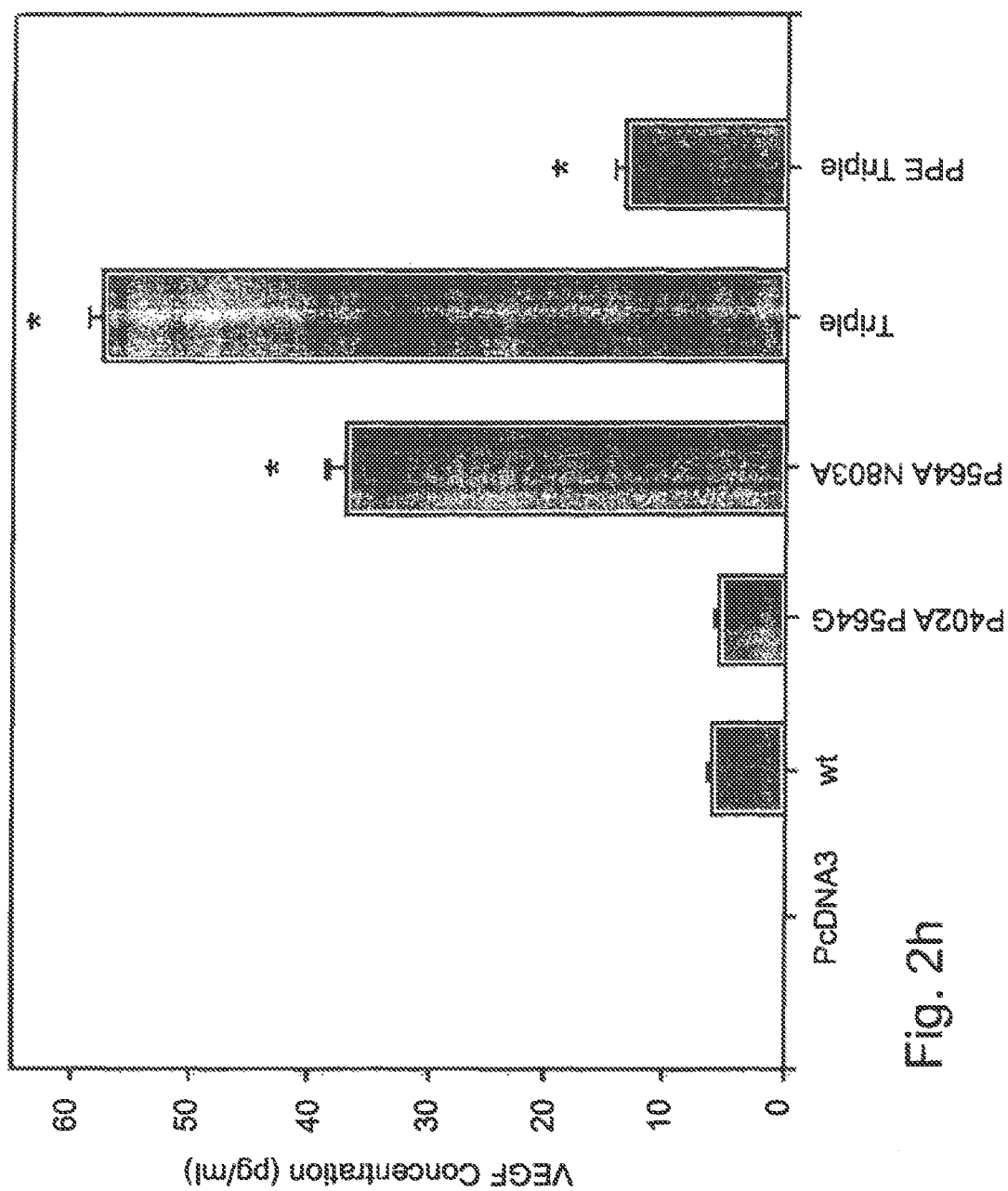

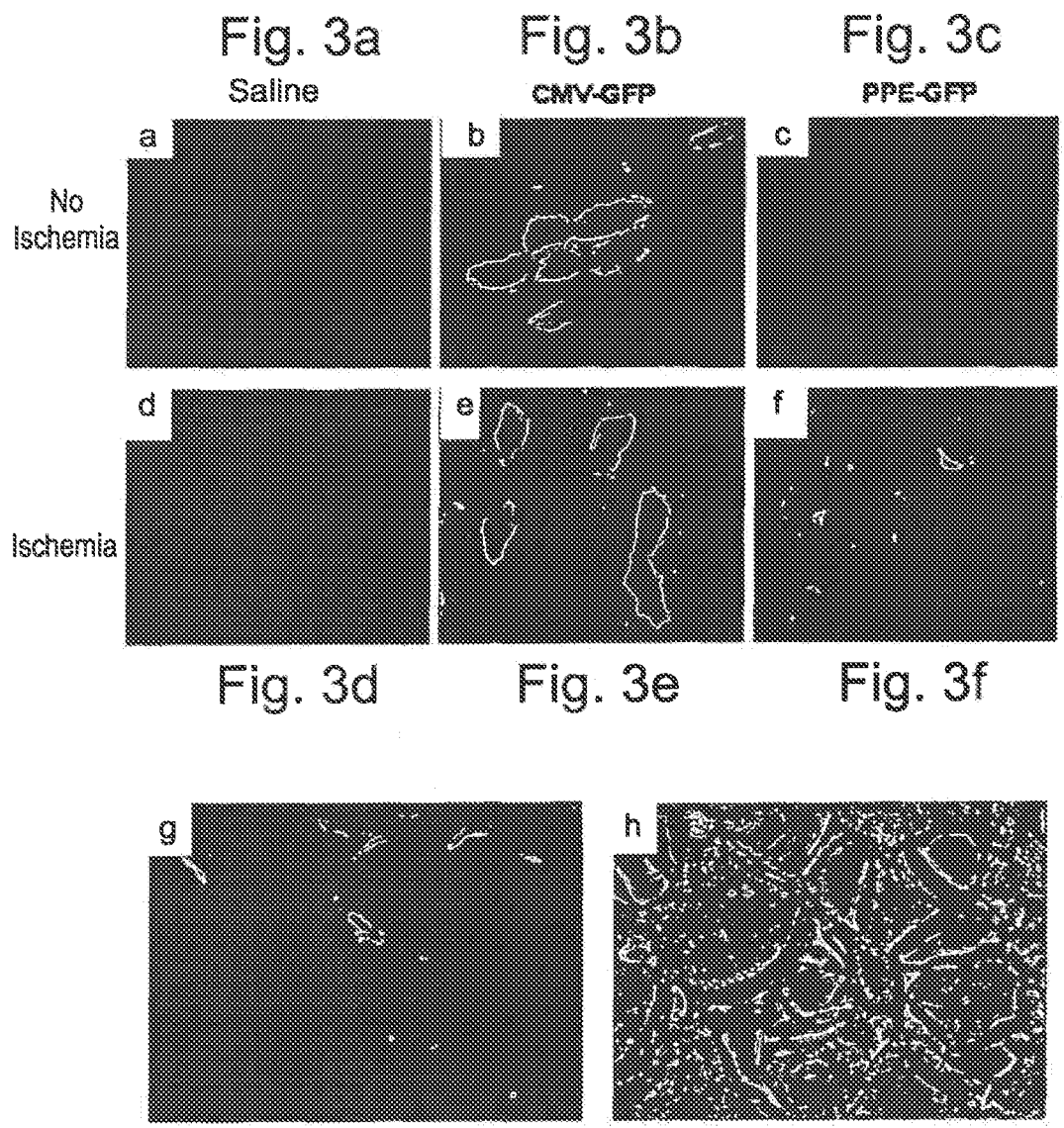

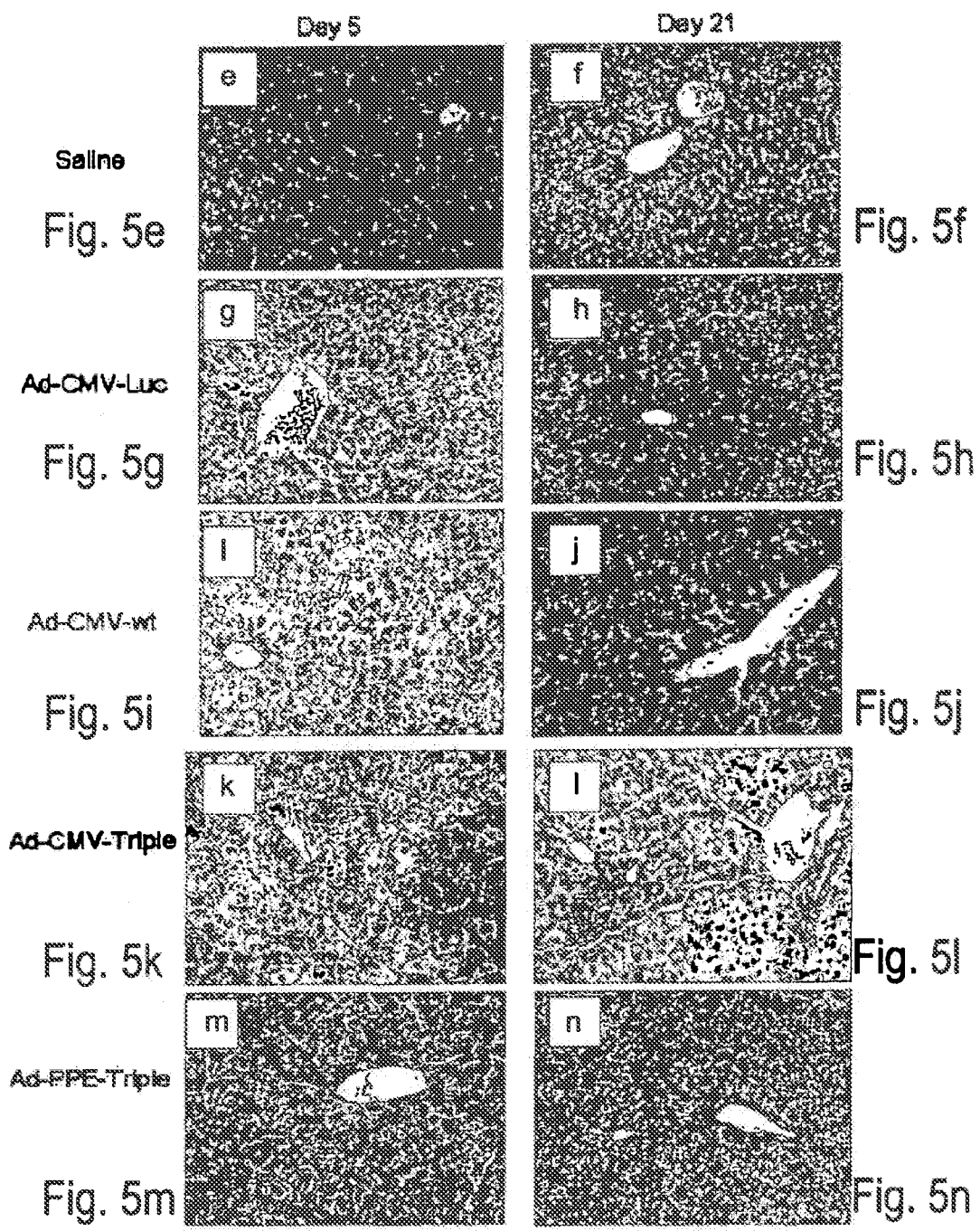

SEQUENCE LISTING

<160> NUMBER OF SEQ ID NOS: 15

<210> SEQ ID NO 1
<211> LENGTH: 2481
<212> TYPE: DNA
<213> ORGANISM: Artificial sequence
<220> FEATURE:
<223> OTHER INFORMATION: Triple mutant HIF-1a coding sequence

<400> SEQUENCE: 1

```
atggagggcg ccggcggcgc gaacgacaag aaaaagataa gttctgaacg tcgaaaagaa      60
aagtctcgag atgcagccag atctcggcga agtaaagaat ctgaagtttt ttatgagctt     120
gctcatcagt tgccacttcc acataatgtg agttcgcatc ttgataaggc ctctgtgatg     180
aggcttacca tcagctattt gcgtgtgagg aaacttctgg atgctggtga tttggatatt     240
gaagatgaca tgaaagcaca gatgaattgc ttttatttga agccttggat ggttttgtt     300 atggttctca cagatgatgg tgacatgatt tacatttctg ataatgtgaa caaatacatg     360
ggattaactc agtttgaact aactggacac agtgtgtttg attttactca tccatgtgac     420
catgaggaaa tgagagaaat gcttacacac agaaatggcc ttgtgaaaaa gggtaaagaa     480
caaaacacac agcgaagctt ttttctcaga atgaagtgta ccctaactag ccgaggaaga     540
actatgaaca taaagtctgc aacatggaag gtattgcact gcacaggcca cattcacgta     600
tatgatacca acagtaacca acctcagtgt gggtataaga accacctat gacctgcttg     660 gtgctgattt gtgaacccat tcctcaccca tcaaatattg aaattccttt agatagcaag     720
actttcctca gtcgacacag cctggatatg aaattttctt attgtgatga agaattacc     780 gaattgatgg gatatgagcc agaagaactt ttaggccgct caattttatga atattatcat     840 gctttggact ctgatcatct gaccaaaact catcatgata tgtttactaa aggacaagtc     900
accacaggac agtacaggat gcttgccaaa agaggtggat atgtctgggt tgaaactcaa     960
gcaactgtca tatataacac caagaattct caaccacagt gcattgtatg tgtgaattac    1020
gttgtgagtg gtattattca gcacgacttg attttctccc ttcaacaaac agaatgtgtc    1080
cttaaaccgg ttgaatcttc agatatgaaa atgactcagc tattcaccaa agttgaatca    1140
gaagatacaa gtagcctctt tgacaaactt aagaaggaac ctgatgcttt aactttgctg    1200
gccgcagccg ctggagacac aatcatatct ttagattttg gcagcaacga cacagaaact    1260
gatgaccagc aacttgagga agtaccatta tataatgatg taatgctccc ctcacccaac    1320
gaaaaattac agaatataaa tttggcaatg tctccattac ccaccgctga acgccaaag    1380 ccacttcgaa gtagtgctga ccctgcactc aatcaagaag ttgcattaaa attagaacca    1440
aatccagagt cactggaact ttcttttacc atgcccccaga ttcaggatca gacacctagt    1500
ccttccgatg aagcactag acaaagttca cctgagccta atagtcccag tgaatattgt    1560
ttttatgtgg atagtgatat ggtcaatgaa ttcaagttgg aattggtaga aaacttttt    1620 gctgaagaca cagaagcaaa gaacccattt tctactcagg acacagattt agacttggag    1680
atgttagctg gctatatccc aatggatgat gacttccagt acgttccttt cgatcagttg    1740
tcaccattag aaagcagttc cgcaagccct gaaagcgcaa gtcctcaaag cacagttaca    1800
gtattccagc agactcaaat acaagaacct actgctaatg ccaccactac cactgccacc    1860
actgatgaat aaaaacagt gacaaaagac cgtatggaag acattaaaat attgattgca    1920
tctccatctc ctacccacat acataaagaa actactagtg ccacatcatc accatataga    1980
gatactcaaa gtcggacagc ctcaccaaac agagcaggaa aaggagtcat agaacagaca    2040
```

```
gaaaaatctc atccaagaag ccctaacgtg ttatctgtcg ctttgagtca aagaactaca    2100
gttcctgagg aagaactaaa tccaaagata ctagctttgc agaatgctca gagaaagcga    2160
aaaatggaac atgatggttc acttttcaa gcagtaggaa ttggaacatt attacagcag     2220
```
(line shown as `aaaatggaac atgatggttc acttttcaa gcagtaggaa ttggaacatt attacagcag`)

```
ccagacgatc atgcagctac tacatcactt tcttggaaac gtgtaaaagg atgcaaatct    2280
agtgaacaga atggaatgga gcaaaagaca attattttaa taccctctga tttagcatgt    2340
agactgctgg ggcaatcaat ggatgaaagt ggattaccac agctgaccag ttatgattgt    2400
gaagttgctg ctcctataca aggcagcaga aacctactgc agggtgaaga attactcaga    2460
gctttggatc aagttaactg a                                              2481
```

<210> SEQ ID NO 2
<211> LENGTH: 826
<212> TYPE: PRT
<213> ORGANISM: Artificial sequence
<220> FEATURE:
<223> OTHER INFORMATION: Triple mutant HIF-1a

<400> SEQUENCE: 2

```
Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
```

```
                275                 280                 285
Lys Thr His His Asp Met Phe Thr Lys Gly Gln Val Thr Gly Gln
290                 295                 300

Tyr Arg Met Leu Ala Lys Arg Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
                355                 360                 365

Met Lys Met Thr Gln Leu Phe Thr Lys Val Glu Ser Glu Asp Thr Ser
370                 375                 380

Ser Leu Phe Asp Lys Leu Lys Lys Glu Pro Asp Ala Leu Thr Leu Leu
385                 390                 395                 400

Ala Ala Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
                420                 425                 430

Asp Val Met Leu Pro Ser Pro Asn Glu Lys Leu Gln Asn Ile Asn Leu
            435                 440                 445

Ala Met Ser Pro Leu Pro Thr Ala Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
                500                 505                 510

Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
530                 535                 540

Glu Ala Lys Asn Pro Phe Ser Thr Gln Asp Thr Asp Leu Asp Leu Glu
545                 550                 555                 560

Met Leu Ala Gly Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
                580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Ala Thr Thr Asp Glu Leu
610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
                675                 680                 685

Asn Val Leu Ser Val Ala Leu Ser Gln Arg Thr Thr Val Pro Glu Glu
            690                 695                 700
```

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
            725                 730                 735

Leu Leu Gln Gln Pro Asp Asp His Ala Ala Thr Thr Ser Leu Ser Trp
        740                 745                 750

Lys Arg Val Lys Gly Cys Lys Ser Ser Glu Gln Asn Gly Met Glu Gln
    755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Ala Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 3
<211> LENGTH: 826
<212> TYPE: PRT
<213> ORGANISM: Homo sapiens

<400> SEQUENCE: 3

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp

```
            245                 250                 255
Glu Arg Ile Thr Glu Leu Met Gly Tyr Glu Pro Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
            325                 330                 335

Cys Val Asn Tyr Val Val Ser Gly Ile Ile Gln His Asp Leu Ile Phe
        340                 345                 350

Ser Leu Gln Gln Thr Glu Cys Val Leu Lys Pro Val Glu Ser Ser Asp
    355                 360                 365

Met Lys Met Thr Gln Leu Phe Thr Lys Val Glu Ser Glu Asp Thr Ser
370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
            405                 410                 415

Asp Thr Glu Thr Asp Asp Gln Gln Leu Glu Glu Val Pro Leu Tyr Asn
        420                 425                 430

Asp Val Met Leu Pro Ser Pro Asn Glu Lys Leu Gln Asn Ile Asn Leu
    435                 440                 445

Ala Met Ser Pro Leu Pro Thr Ala Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
            485                 490                 495

Gln Thr Pro Ser Pro Ser Asp Gly Ser Thr Arg Gln Ser Ser Pro Glu
        500                 505                 510

Pro Asn Ser Pro Ser Glu Tyr Cys Phe Tyr Val Asp Ser Asp Met Val
    515                 520                 525

Asn Glu Phe Lys Leu Glu Leu Val Glu Lys Leu Phe Ala Glu Asp Thr
530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
            565                 570                 575

Phe Asp Gln Leu Ser Pro Leu Glu Ser Ser Ser Ala Ser Pro Glu Ser
        580                 585                 590

Ala Ser Pro Gln Ser Thr Val Thr Val Phe Gln Gln Thr Gln Ile Gln
    595                 600                 605

Glu Pro Thr Ala Asn Ala Thr Thr Thr Thr Ala Thr Thr Asp Glu Leu
610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
            645                 650                 655

Ser Pro Tyr Arg Asp Thr Gln Ser Arg Thr Ala Ser Pro Asn Arg Ala
        660                 665                 670
```

```
Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
        690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 4
<211> LENGTH: 978
<212> TYPE: DNA
<213> ORGANISM: Artificial sequence
<220> FEATURE:
<223> OTHER INFORMATION: PPE-1 promoter

<400> SEQUENCE: 4
acgtgtactt ctgatcggcg atactaggga gataaggatg tacctgacaa aaccacattg      60
ttgttgttat cattattatt tagttttcct tccttgctaa ctcctgacgg aatctttctc     120
acctcaaatg cgaagtactt tagtttagaa aagacttggt ggaaggggtg gtggtggaaa     180
agtagggtga tcttccaaac taatctggtt ccccgcccgc cccagtagct gggattcaag     240
agcgaagagt ggggatcgtc cccttgtttg atcagaaaga cataaaagga aaatcaagtg     300
aacaatgatc agccccacct ccaccccacc ccctgcgcg cgcacaatac aatctattta      360
attgtacttc atacttttca ttccaatggg gtgactttgc ttctggagaa actcttgatt     420
cttgaactct ggggctggca gctagcctcc agaagcaaag tcaccccatt ggaatgaaaa     480
gtatgaagta caatgaaaag tatgaagtac tggctccaga agcaaagtca ccctccagaa     540
gcaaagtcac cccattggaa tgaaaagtat gaagtacgct agcaaaggg gaagcgggct      600 gctgctctct gcaggttctg cagcggtctc tgtctagtgg gtgttttctt tttcttagcc     660
ctgcccctgg attgtcagac ggcgggcgtc tgcctctgaa gttagccgtg atttcctcta     720
gagccgggtc ttatctctgg ctgcacgttg cctgtgggtg actaatcaca caataacatt     780
gtttagggct ggaataaagt cagagctgtt taccccact ctataggggt tcaatataaa      840
aaggcggcgg agaactgtcc gagtcagaag cgttcctgca ccggcgctga gagcctgacc     900
cggtctgctc cgctgtcctt gcgcgctgcc tcccggctgc ccgcgacgct ttcgccccag     960
tggaagggcc acttgctg                                                  978

<210> SEQ ID NO 5
<211> LENGTH: 6
<212> TYPE: DNA
```

```
<213> ORGANISM: Artificial sequence
<220> FEATURE:
<223> OTHER INFORMATION: Hypoxia response element

<400> SEQUENCE: 5 gcacgt                                                                          6

<210> SEQ ID NO 6
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 6
gtcggacagc ctcaccaaac agag                                                     24

<210> SEQ ID NO 7
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 7
gttaacttga tccaaagctc tgag                                                     24

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
cacgtggttc acctcagcac                                                          20

<210> SEQ ID NO 9
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 9
cagcgatttc ttccaagcg                                                           19

<210> SEQ ID NO 10
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 10
cagcgcagct actgccatcc aatcgaga                                                 28

<210> SEQ ID NO 11
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 11
gcttgtcaca tctgcaagta cgttcgttta                                               30
```

```
<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
atcgccgagt gcaagacgcg                                          20

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
aagcaccatt ggccgtccga                                          20

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
accacagtcc atgccatcac                                          20

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
tccaccaccc tgttgctgta                                          20
```

ENDOTHELIAL CELL-SPECIFIC POLYNUCLEOTIDES AND USE THEREOF

RELATED APPLICATIONS

This application is a divisional of U.S. patent application Ser. No. 13/163,776, filed on Jun. 20, 2011, which is a divisional of U.S. patent application Ser. No. 12/309,856, 371(c) date of Feb. 2, 2009, which is the National Phase of PCT Patent Application No. PCT/IL2007/000959 having international filing date of Jul. 31, 2007, which claims the benefit of priority of U.S. Provisional Patent Application No. 60/834,157 filed on Jul. 31, 2006. The contents of the above applications are all incorporated herein by reference in their entireties.

REFERENCE TO SEQUENCE LISTING SUBMITTED ELECTRONICALLY VIA EFS-WEB

The content of the electronically submitted sequence listing (Name: 3182_0400003_Sequence_Listing_ascii.txt; Size: 21,663 bytes; and Date of Creation: Sep. 23, 2014) filed with the application is incorporated herein by reference in its entirety.

FIELD AND BACKGROUND OF THE INVENTION

The present invention relates to polypeptides and polynucleotides encoding same and use thereof in the treatment of medical conditions associated with ischemia.

Angiogenesis is the budding of new blood vessels from pre-existing ones. It occurs in various physiological conditions such as the female reproductive cycle, as well as pathological conditions which include tumors, tissue ischemia and wound healing.

Ischemic heart disease is the leading cause of mortality in many industrialized countries and is responsible for over 500,000 deaths in the US alone each year. Current treatment options include drug therapy, coronary angioplasty and the more invasive coronary artery bypass grafting (CABG).

However, in all these cases, technical issues including the size of the artery involved, lack of appropriate distal vasculature, the complexity of the arterial lesions that cause the occlusion, and the general clinical conditions of the patient frequently prevent revascularization of the ischemic tissues.

A less invasive approach which has recently been developed is therapeutic angiogenesis. This term refers to the introduction of proangiogenic factors aimed at enhancing neovascularization of the ischemic tissue, thus alleviating the ischemia. Two main methods have been utilized in the field of therapeutic angiogenesis; the first is angiogenic gene therapy either in the form of naked DNA or with viral vehicles to deliver various cytokines, the most commonly used being Vascular Endothelial Growth Factor (VEGF) and Fibroblast Growth Factor (FGF). A more recent method is cell therapy with fully differentiated cells, endothelial progenitor cells or mesenchymal stem cells. Both methods have shown success in animal models and early phase clinical trials.

However, many obstacles still have to be overcome before therapeutic angiogenesis becomes a real clinical alternative for patients suffering from ischemic diseases.

For angiogenic gene therapy, these obstacles include the need for tissue specificity of transgene expression, choice of delivery vehicle, optimization of dose and timing, optimization of route of administration and the potential of adverse events such as edema and tumor development.

Another limitation to the success of angiogenic gene therapy is the lack of maturation of the newly formed vessels and their subsequent regression, thus preventing a significant long-lasting therapeutic effect. This may be because the delivered angiogenic genes are expressed only for a relatively short period of time which does not allow for vessel maturation and recruitment of smooth muscle cells to take place or because multiple angiogenic factors are required for vessel maturation to occur. A possible solution is to use an upstream angiogenic regulator which would activate multiple angiogenic factors simultaneously, thus more closely resembling physiological angiogenesis. Such a factor is hypoxia-inducible factor 1 (HIF-1).

Hypoxia Inducible Factor-1 (HIF-1) is a transcription factor and a master regulator of the response to oxygen deprivation, activating over 40 genes during hypoxia. It is a heterodimeric transcription factor consisting of two subunits; the subunit α is subject to tight regulation by the level of oxygen and is induced during hypoxia, whereas subunit β is constitutively expressed regardless of oxygen tension.

HIF-1α contains two transactivation domains (N-TAD and C-TAD) and an oxygen-dependent degradation domain (ODDD). The protein von-Hippel-Lindau (VHL) interacts with the ODDD of HIF-1α under normoxic conditions and acts as part of an E3-ubiquitin ligase complex, thus sending HIF-1α to proteosomal degradation. In hypoxia, HIF-1α dimerizes with HIF-1β and activates the transcription of its target genes in the nucleus.

Recently, it was shown that the interaction of VHL with HIF-1α is enabled by prolyl hydroxylation of two specific residues within the HIF-1α protein (Epstein, A. C. et al. 2001, *Cell* 107, 43-54. Masson, N., et al. 2001, *Embo J* 20, 5197-206).

Three prolyl hydroxylases (PHD 1-3) were found to hydroxylate HIF-1α during normoxia. PHD 1 and 2 hydroxylate at residues 402 and 564 whereas PHD 3 hydroxylates at residue 564 only.

A second mechanism of regulation of HIF-1α was uncovered in 2002 (Lando, D et al, 2002, *Science* 295, 858-61) and includes the asparaginyl hydroxylation of HIF-1α at residue 803, effected by an asparaginyl hydroxylase, also termed Factor Inhibiting HIF-1 (FIH-1). This hydroxylation prevents the interaction of HIF-1α with the co-factor p300, thus hindering the transcriptional activity of HIF-1α.

Hence, during normoxia two mechanisms of regulation are responsible for the decrease in HIF-1α activity, one concerning its stability via prolyl hydroxylations and the other concerning its transcriptional activation via asparaginyl hydroxylation.

These prolyl and asparaginyl hydroxylases are all dioxygenases which are 2-oxoglutarate and iron dependent and their requirement for cellular oxygen could provide the basis for their activity as oxygen sensors.

Two specific point mutations at residues 402 and 564 were demonstrated to abolish the interaction of HIF-1α with VHL, thus rendering HIF-1α constitutively stable (Masson et al., 2001, *Embo J* 20, 5197-206). The resultant mutant HIF-1α was as active as hypoxia treatment in driving the expression of an HRE-Luciferase construct. Two mutations at residues 564 and 803 were shown to give HIF-1α full transcriptional activity, similar to that obtained by treatment with the hypoxia mimetic iron chelator 2,2'-Dipyridyl (Lando et al., 2002, *Science* 295, 858-61).

Transgenic mice overexpressing a mutant hHIF-1α in which residues 401 to 602 are deleted, under the regulation of Keratin 14 promoter showed increased vascularization in the skin (Elson, D. A. et al. 2001, *Genes Dev* 15, 2520-32). These mice showed up-regulation of mRNA of Glut-1 and VEGF, known targets of HIF-1α. In comparison with VEGF overexpressing mice, these mice had blood vessels which were less leaky and showed greater maturity. This may be explained by the fact that HIF-1α induces the activation of multiple angiogenic factors (i.e. erythropoietin), similar to the physiological angiogenic response, in contrast to VEGF alone. In addition, HIF-1α induces the activation of many isoforms of VEGF and other genes, again more closely resembling the physiological response, which could not be achieved by the administration of a single isoform.

A constitutively active form of HIF-1α was first tested in angiogenic gene therapy in 2000 (Vincent, K. A. et al. 2000, *Circulation* 102, 2255-61). It contained the DNA binding domain and dimerization domains of HIF-1α attached to the transactivation domain VP16 of the Herpes Simplex Virus (HSV) under the regulation of CMV promoter. The resultant mutant was able to induce HIF target genes in-vitro. When administered locally as naked DNA it caused increased capillary density and blood perfusion in a mouse hindlimb ischemia model. The same construct also showed therapeutic effect when injected IM in a rat MI model (Shyu, K. G. et al, 2002, *Cardiovasc Res* 54, 576-83).

An adenovirus expressing a constitutively active mutant HIF-1α, with a deletion of residues 401-602, under the regulation of CMV promoter was able to induce angiogenesis in the non-ischemic tissue of the retina (Kelly, B. D. et al, 2003 *Circ Res* 93, 1074-81).

The two constructs mentioned above bear large deletions of the HIF-1α molecule, and lack one or both of the native HIF-1α transactivation domains (N-TAD and C-TAD), which may result in reduced activation potential and specificity of HIF-1α. In addition, HIF-1α is expressed in these constructs under the regulation of CMV, a versatile and non-specific promoter, which may limit its application due to non-specific expression and potential side-effects.

Various routes of administration have been used to deliver the therapeutic gene to the ischemic region, including intravascular and intramuscular in the case of peripheral ischemia, and intramyocardial, intrapericardial and intracoronary in the case of myocardial ischemia. The intravenous route confers advantages which include easy access without the need for an invasive procedure, technical safety and low cost as well as accessibility to a large patient population. However, despite its obvious clinical appeal, the use of this administration route is uncommon due to systemic distribution of the vector leading to low transgene expression in the target organ along with unwanted expression in non-target organs resulting in systemic side-effects, which limit the dose that may be administered. This limitation, in turn, tends to restrict the efficacy of the treatment. Unwanted expression of a pro-angiogeneic gene could induce pathological angiogenesis, possibly leading to tumor development and retinopathy, and may therefore be unacceptable. Thus, the ability to direct transgene expression specifically to the ischemic target organ is of outmost importance for systemic administration to be efficacious and safe.

There is thus a widely recognized need for, and it would be highly advantageous to have pro-angiogenic factors together with safe and effective methods of delivering same.

SUMMARY OF THE INVENTION

According to one aspect of the present invention there is provided an isolated polynucleotide comprising a nucleic acid sequence encoding a polypeptide having an amino acid sequence of HIF-1α, the polypeptide being stably expressed and constitutively active.

According to further features in preferred embodiments of the invention described below, the nucleic acid sequence is as set forth in SEQ ID NO:1.

According to still further features in the described preferred embodiments the amino acid sequence is as set forth in SEQ ID NO: 2.

According to still further features in the described preferred embodiments the amino acid sequence being at least 90% homologous to SEQ ID NO: 3 and comprising a mutation at a position corresponding to proline 402 of SEQ ID NO: 3, a mutation at a position corresponding to proline at 564 of SEQ ID NO: 3 and a mutation at a position corresponding to asparagine 803 of SEQ ID NO: 3.

According to another aspect of the present invention there is provided an isolated polypeptide comprising an amino acid sequence encoding a polypeptide having a HIF-1α amino acid sequence, the polypeptide being stably expressed and constitutively active.

According to still further features in the described preferred embodiments the amino acid sequence is as set forth in SEQ ID NO: 2.

According to still further features in the described preferred embodiments the amino acid sequence being at least 90% homologous to SEQ ID NO: 3 and comprising a mutation at a position corresponding to proline 402 of SEQ ID NO: 3, a mutation at a position corresponding to proline at 564 of SEQ ID NO: 3 and a mutation at a position corresponding to asparagine 803 of SEQ ID NO: 3.

According to another aspect of the present invention there is provided a nucleic acid construct comprising the polynucleotide of the present invention.

According to still further features in the described preferred embodiments the nucleic acid construct further comprising a cis-regulatory element.

According to still further features in the described preferred embodiments the cis-regulatory element comprises a promoter element.

According to still further features in the described preferred embodiments the promoter element is an endothelial specific promoter element.

According to still further features in the described preferred embodiments the endothelial specific promoter element comprises at least one copy of the PPE-1 promoter.

According to still further features in the described preferred embodiments the PPE-1 promoter is as set forth in SEQ ID NO: 4.

According to still further features in the described preferred embodiments the cis-regulatory element further comprises a hypoxia response element.

According to yet another aspect of the present invention there is provided a cell comprising the nucleic acid construct.

According to still another aspect of the present invention there is provided a pharmaceutical composition comprising as an active agent the nucleic acid construct and a pharmaceutically acceptable carrier.

According to an additional aspect of the present invention there is provided a method of treating a medical condition associated with hypoxia or ischemia, reduced tissue perfusion inclusion or 'low flow', the method comprising administering to a subject in need thereof a therapeutically effective amount of an agent capable of upregulating the polypeptide of the present invention in cells of the subject, thereby treating an angiogenesis-related disease.

According to still further features in the described preferred embodiments the agent is the polypeptide.

According to still further features in the described preferred embodiments the agent is the nucleic acid construct.

According to still further features in the described preferred embodiments the administering is effected systemically.

According to still further features in the described preferred embodiments the disease or condition associated with ischemia is selected from the group consisting of wound healing, ischemic stroke, ischemic heart disease, peripheral vascular disease, renal artery disease, gastrointestinal lesions, burns, skin transplantation, vascular grafts, organ repair, bone reparative disorders, liver disorders, uterine disorders, ocular angiogenesis disorders, bone regeneration disorders, cartilage repair disorders and smooth muscle cell disorders.

The present invention successfully addresses the shortcomings of the presently known configurations by providing novel treatments for medical conditions associated with ischemia.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1C is an RT-PCR analysis of mRNA isolated from HeLa cells 48 hours post-transfection with HIF-1α plasmids or pcDNA3 control. Treatment with 2,2'-dipyridyl (2,2'-DP) is illustrated in FIG. 1D. HRE-mediated transcription was measured in VHL-deficient renal cell carcinoma cells following co-transfection of p2.1 HRE-luc with different HIF-1α plasmids or pcDNA3 control. Data are expressed as luciferase ratios and are normalized to β-gal (mean±S.D). *p<0.001 and +p=0.003 vs. P402A P564G mutant. HEK293 cells were co-transfected with p2.1 HRE-luciferase, HIF-1α plasmids and the indicated amount of FIH-1 antisense (FIG. 1E). Data are expressed as luciferase ratios and are normalized to β-gal (mean±S.D).

FIGS. 2A-H are photographs and bar graphs illustrating that the triple mutant HIF-1α shows greater angiogenic potency than P402A P564G and P564A N803A double mutants. FIGS. 2A-F are representative photographs of an in-vitro angiogenesis assay in HUVECs transfected with pcDNA3 (FIG. 2A), wt-HIF-1α (FIG. 2B), P402A P564G (FIG. 2C), P564A N803A (FIG. 2D), Triple mutant (FIG. 2E) or VEGF (FIG. 2F). FIG. 2G is a bar graph illustrating tube formation of transfected HUVECs, which was quantified by counting the number of capillary branches per high power microscopic field. Results are expressed as mean±S.D of 5 random microscopic fields. FIG. 2H is a bar graph illustrating VEOF protein concentration of transfected HUVECs, as determined by ELISA and results are expressed as mean±S.D. *p=0.029 vs. P402A P564G.

FIGS. 3A-H are photographs of fluorescent microscope sections illustrating the endothelial and ischemia specificity of PPE1-3x promoter. FIGS. 3A-F illustrate fluoresent microscopic sections of gastrocnemius muscles of mice subjected to either hindlimb ischemia or sham procedure, which were injected systemically via the tail vein 7 days later with either saline (FIGS. 3A and 3D), Ad-CMV-GFP (FIGS. 3B and 3E), or Ad-PPE1-3x-GFP (FIGS. 3C and 3F). FIGS. 3G-H illustrate sections of gastrocnendus muscle of mouse treated with Ad-PPE-1-3x-GFP as seen in fluorescent microscopy (FIG. 3G) or phase microscopy (FIG. 3H) showing erythrocytes within a capillary (arrows) made of GFP expressing endothelial cells (arrowhead).

FIG. 4A is a line graph of Blood flow in the ischemic limb measured immediately following and at 7, 14, 21 and 28 days after left femoral artery ligation. Data are expressed as the ratio of the left (ischemic) to right (non-ischemic) limb perfusion. Saline, n=8; Ad-CMV-Luc, n=11; Ad-CMV-wt, n=11; Ad-CMV-Triple, n=12; Ad-PPE-Triple, n=11. FIG. 4B are representative laser Doppler blood flow images of the ischemic (left) and non-ischemic (right) limbs at day 28 post-surgery. In color-coded images, normal perfusion is depicted in red while low and/or no perfusion in blue. FIG. 4C are representative photos of mouse hindlimbs 21 days post-surgery. FIG. 4D is a bar graph illustrating the percentage of mice showing toe necrosis by day 21 post-surgery. FIGS. 4E-F illustrate representative CD31 staining (FIG. 4E) and quantitation (FIG. 4F) of capillaries from sections of gastrocnemius muscles 28 days following femoral artery ligation. *p<0.01.

FIGS. 5A-N illustrate that Ad-PPE-Triple is less toxic than Ad-CMV-Triple following systemic administration. FIG. 5A is a point graph illustrating the changes in mice body weights over time following systemic injection of saline or adenovirus. FIGS. 5E-N are histological sections of mice livers 5 (FIGS. 5E, G, I, K and M) and 21 days (FIGS. 5F, H, J, L and N) following systemic injection of saline (FIGS. 5E-F), AdCMV-Luc (FIGS. 5G-H), AdCMV-wt (FIGS. 5I-J), AdCMV-triple (FIGS. 5K-L), AdPPE-triple (FIGS. 5M-N).

FIG. 6A is a point graph of blood flow in the ischemic limb measured immediately following and at 7, 14, 21 and 28 days after left femoral artery resection. Data are expressed as the ratio of the left (ischemic) to right (non-ischemic) limb perfusion. Saline, n=9; Ad-CMV-Luc, n=8; Ad-CMV-wt, n=9; Ad-CMV-Triple, n=7; Ad-PPE-Triple, n=8. FIG. 6B is a bar graph illustrating the percentage of mice showing toe necrosis by day 21 post-surgery. FIG. 6C illustrate representative photos of mice hindlimbs 21 days post-surgery. FIG. 6D are representative laser Doppler blood flow images of the ischemic (left) and non-ischemic (right) limbs at day 28 post-surgery. In color-coded images, normal perfusion is depicted in red while low and/or no perfusion in blue. FIGS. 6E-F illustrate representative CD31 staining (FIG. 6E) and quantitation (FIG. 6F) of capillaries from sections of gastrocnemius muscles 28 days after femoral artery ligation. *p<0.01.

DESCRIPTION OF THE PREFERRED EMBODIMENTS

The present invention is of HIF-1α polypeptides and polynucleotides encoding same, pharmaceutical compositions which comprise the same and methods of producing and using same.

Specifically, the present invention can be used in the treatment of diseases associated with ischemia.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Hypoxia-inducible factor 1α (HIF-1α) is a heterodimeric transcription factor and a key regulator of the response to low oxygen levels, and has been suggested as a potential candidate for therapeutic angiogenesis. Stabilization of HIF-1α may be achieved by point mutations P402A and P5640 [Masson et al., 2001, Embo J 20, 5197-206] while constitutive activity of its C-transactivation domain (C-TAD) is achieved by point mutation N803A [Lando et al., 2002, Science 295, 858-61].

Figure 1A:
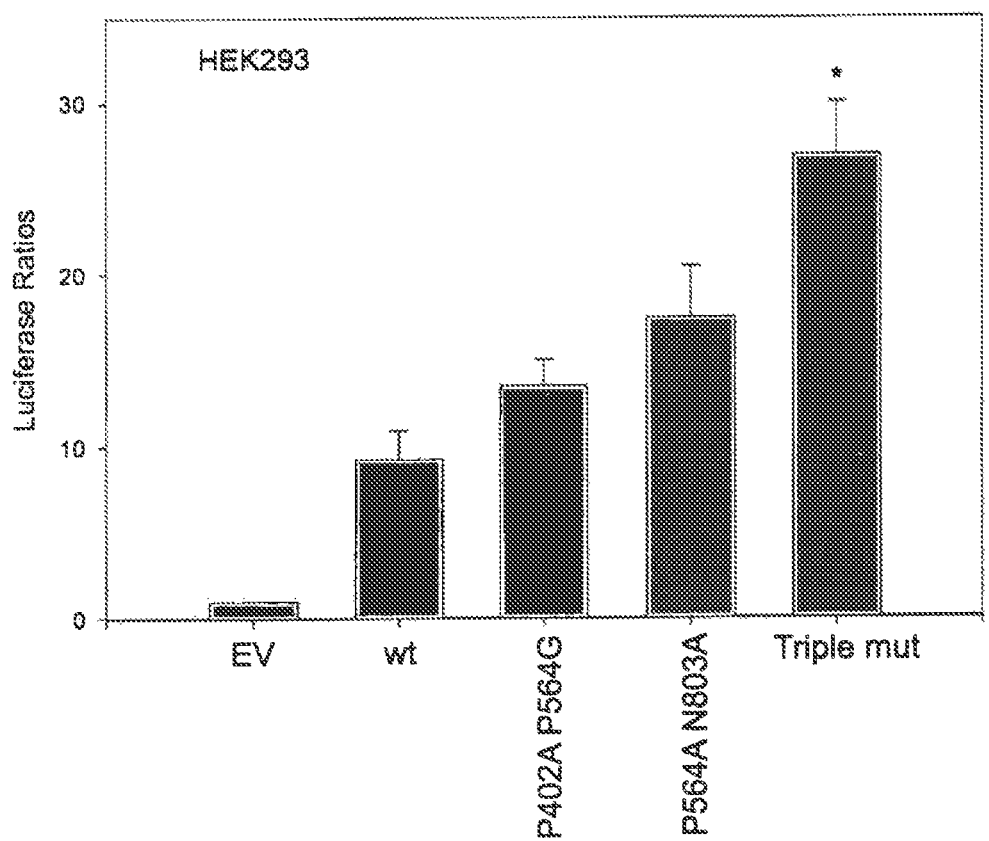
FIGS. 1A-E are bar graphs and photographs illustrating the transcriptional activity of the triple mutant HIF-1α as compared to the P402A P564G and P564A N803A double mutants. HRE-mediated transcription was measured in HEK293 (FIG. 1A) and BAEC (FIG. 1B) following co-transfection of p2.1 HRE-luc with different HIF-1α plasmids or pcDNA3 control. Data are expressed as luciferase ratios and are normalized to β-gal (mean±S.D). *p<0.001 compared with double mutants.
Figure 1B:
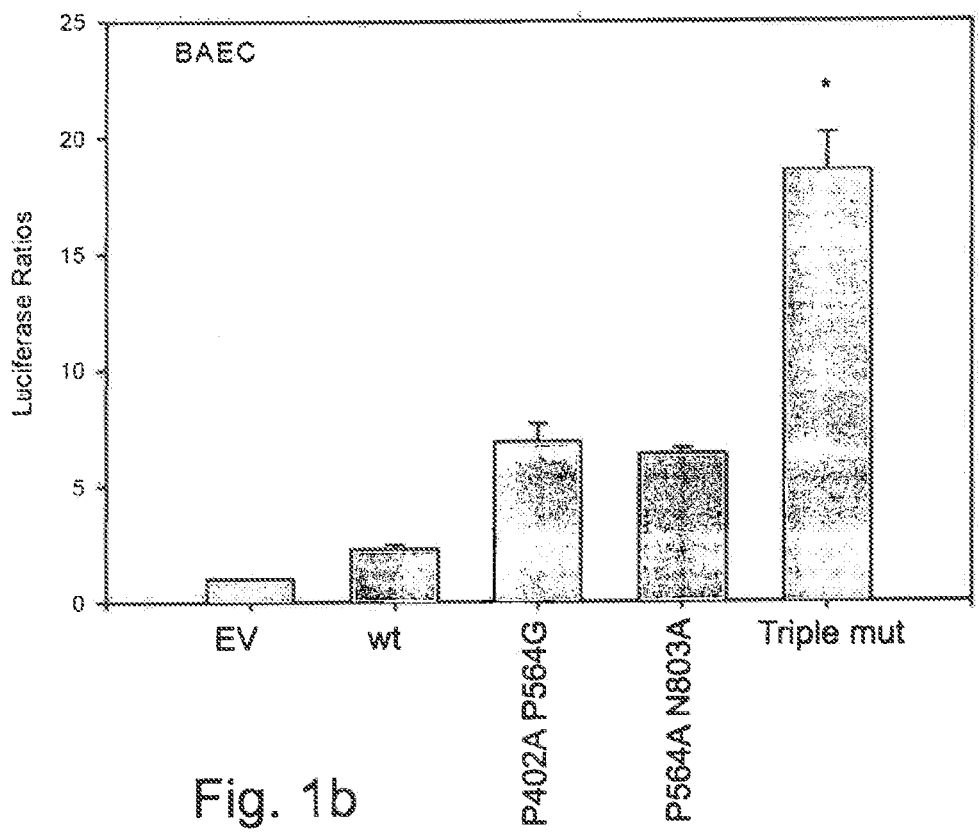

While reducing the present invention to practice the present inventors genetically engineered a mutant form of HIF-1α combining the three point mutations P402A P564G N803A (triple mutant), rendering HIF-1α both stable and constitutively active. Surprisingly, the triple mutant showed a synergistic effect on the expression of a reporter gene linked to a hypoxia response element as compared to the two known double mutant forms of HIF-1α, as illustrated in FIGS. 1A-B. Thus, the present inventors showed that constitutive activation of the HIF-1α C-transactivation domain, and not merely stabilization of the HIF-1α molecule, is essential for optimal HIF-mediated transcription and proangiogenic effects. Accordingly, the triple mutant HIF-1α, or polynucleotide encoding same, of the present invention can be used to treat diseases or conditions associated with angiogenesis.

Figure 2G:
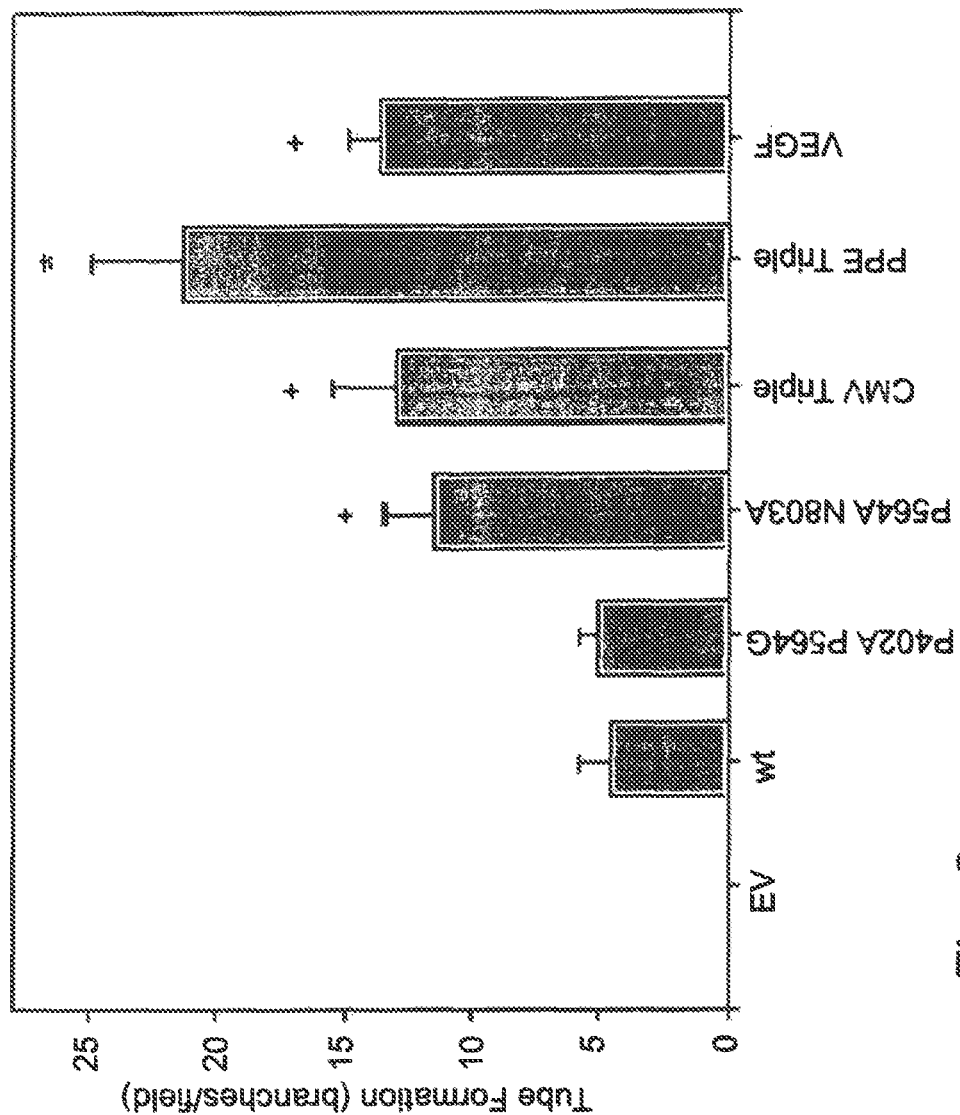

As illustrated in FIGS. 2G-H, the triple mutant of the present invention shows a greater angiogenic potency than P402A P564G and P564A N803A double mutants as demonstrated in in-vitro angiogenesis assays. Furthermore, as illustrated in FIGS. 4A-F, an adenovirus expressing the triple mutant HIF-1α of the present invention showed enhanced blood perfusion and increased capillary density compared with an adenovirus expressing wild-type HIF-1α and controls in a mouse hindlimb ischemic model. A modified preproendothelin-1 promoter was shown to allow specific expression in ischaemic endothelial cells (FIGS. 3C and 3F). Expression of the triple mutant HIF-1α under the regulation of such a promoter reduced ectopic expression and systemic side-effects as compared to expression of the triple mutant under the control of a constitutively active promoter (FIGS. 5A-N and 6A-D).

Thus, according to one aspect of the present invention, there is provided an isolated polypeptide comprising an amino acid sequence encoding a polypeptide having a HIF-1α amino acid sequence, the polypeptide being stably expressed and constitutively active.

As used herein, the phrase "HIF-1α" refers to at least an active portion of HIF-1α (i.e., a portion having HIF-1α activity). Preferably the HIF-1α of the present invention is human HIF-1α, e.g. GenBank Accession No: NM001530.

As used herein the phrase "HIF-1α activity" refers to at least the transcription factor activity of HIF-1α i.e., the ability of HIF-1α to transcriptionally up-regulate target angiogenic genes. In order to function as a transcription factor, HIF-1α, dimerizes with HIF-1β and binds co-factors such as P300. Accordingly the HIF-1α of the present invention preferably comprises a functional DNA binding domain and functional co-factor and HIF-1β binding domains. The HIF-1α of the present invention does not have to comprise for example amino or carboxy terminal amino acids since these terminal sequences are not required for HIF-1α activity.

As used herein, the phrase "constitutively active" refers to HIF-1α which comprises transcriptional activity which is not regulated by the hypoxic state of the cell.

As used herein, the phrase "stably expressed" refers to a polypeptide which is not subject to an increase in proteosomal degradation in response to hypoxia. Accordingly the half life of the polypeptide is not altered by the presence of Von-Hippel-Lindau (VHL). Preferably, the half life of the polypeptides of the present invention are at least about 2 times greater, and even more preferably 5 times the half life of the wild type polypeptides (i.e. not comprising a mutation).

According to a preferred embodiment of this aspect of the present invention, the polypeptide of the present invention is at least 50% homologous, more preferably at least 60% homologous, more preferably at least 70% homologous, more preferably at least 80% homologous, and most preferably at least 90% homologous to SEQ ID NO: 3 and comprises a mutation at a position corresponding to proline 402 of SEQ ID NO: 3, a mutation at a position corresponding to proline at 564 of SEQ ID NO: 3 and a mutation at a position corresponding to asparagine 803 of SEQ ID NO: 3.

As used herein, the term "mutation" refers to an alteration in an amino acid sequence compared to the wild type sequence (GenBank Accession No: NM001530 (GI: 31077212)

The mutation may comprise a deletion or a substitution. Exemplary mutations include an alanine corresponding to proline at position 402, a glycine corresponding to proline at position 564 and an alanine corresponding to asparagine at position 803.

Thus, according to a preferred embodiment the polypeptide of the present invention is as set forth in SEQ ID NO: 2.

In addition, the polypeptide of the present invention may comprise other conservative variations of SEQ ID NO: 3.

The phrase "conservative variation" as used herein refers to the replacement of an amino acid residue by another, biologically similar residue. Examples of conservative variations include the substitution of one hydrophobic residue such as isoleucine, valine, leucine, or methionine for another, or the substitution of one solar residue for another, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Methods of protein engineering e.g. display techniques may be used to uncover other mutations which impart stability and constitutive activity to the HIF-1α of the present invention as well as active portions of HIF-1α.

Methods of constructing display libraries are well known in the art. Such methods are described in, for example, Young A C, et al., "The three-dimensional structures of a polysaccharide binding antibody to *Cryptococcus neoformans* and its complex with a peptide from a phage display library: implications for the identification of peptide mimotopes" J Mol Biol 1997 Dec. 12; 274(4):622-34; Giebel L B et al. "Screening of cyclic peptide phage libraries identifies ligands that bind streptavidin with high affinities" Biochemistry 1995 Nov. 28; 34(47):15430-5; Davies E L et al., "Selection of specific phage-display antibodies using libraries derived from chicken immunoglobulin genes" J Immunol Methods 1995 Oct. 12; 186(1):125-35; Jones C R T al. "Current trends in molecular recognition and bioseparation" J Chromatogr A 1995 Jul. 14; 707(1):3-22; Deng S J et al. "Basis for selection of improved carbohydrate-binding single-chain antibodies from synthetic gene libraries" Proc Natl Acad Sci USA 1995 May 23; 92(11):4992-6; and Deng S J et al. "Selection of antibody single-chain variable fragments with improved carbohydrate binding by phage display" J Biol Chem 1994 Apr. 1; 269(13):9533-8, which are incorporated herein by reference.

Other mutations which impart stability and constitutive activity to the HIF-1α of the present invention can also be uncovered using computational biology. For example, various mutated HIF-1α peptide sequences can be computationally analyzed for an ability to impart stability and constitutive activity using a variety of three dimensional computational tools. Software programs useful for displaying three-dimensional structural models, such as RIBBONS (Carson, M., 1997. Methods in Enzymology 277, 25), O (Jones, T A. et al., 1991. Acta Crystallogr. A47, 110), DINO (DINO: Visualizing Structural Biology (2001) http://www.dino3d.org); and QUANTA, INSIGHT, SYBYL, MACROMODE, ICM, MOLMOL, RASMOL and GRASP (reviewed in Kraulis, J., 1991. Appl Crystallogr. 24, 946) can be utilized to model prospective mutant peptide sequences to identify useful mutations.

The term "polypeptide" as used herein encompasses native polypeptides (either degradation products, synthetically synthesized polypeptides or recombinant polypeptides) and peptidomimetics (typically, synthetically synthesized polypeptides), as well as as peptoids and semipeptoids which are polypeptide analogs, which may have, for example, modifications rendering the polypeptides more stable while in a body or more capable of penetrating into cells. Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C (R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |

TABLE 1-continued

| Amino Acid | Three-Letter Abbreviation | One-letter Symbol |
|---|---|---|
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methlbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutvric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methtlhistidine | Nmhis |
| cyclopentylalanine | Cpen | L-N-methylisolleucine | Nmile |
| D-alanine | Dal | L-N-methylleucine | Nmleu |
| D-arginine | Darg | LN-rnethyllysine | Nmlys |
| D-aspartic acid | Dasp | L N methylmethionine | Nmmet |
| D-cysteine | Deys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptohan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-ethylcyclohexylalanine | Mchexa |
| D-α-methylarginine | Dmarg | α-methylcyclopentylalanine | Mcpen |
| D-α-methylaspargine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmieu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenyl-alanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |

TABLE 2-continued

| Non-conventional amino acid | Code | Non-conventional amino acid | Code |
|---|---|---|---|
| D-α-methyltryptophan | Dmtrp | N-cyclohexylglcyine | Nchex |
| D-α-methyltyrosine | Dmty | N-cyclodexlglycine | Ncdec |
| D-α-methylvaline | Dmval | N-cyclododeclglycine | Ncdod |
| D-α-methylainine | Dnmala | N-cycloctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-γ-aminobutyrate | Nmgabu |
| D-N-methylcyclo-hexylalanine | Nmchexa | D-N-methylmethionine | Dnmmet |
| D-N-methylomithine | Dnmorn | N-methylcyclo-pentylalanine | Nmcpen |
| N-methylglycine | Nala | D-N-methylphenylalanine | Dnmphe |
| N-methylamino-isobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-thylgutamine | Mgln | L-α-methylglutamate | Mglu |
| L-α-methylhistidine | Mhis | L-α-methylhomo-phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolyethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclo-hexylalanine | Nmchexa | D-N-methylmethionine | Dnmmet |
| D-N-methylornithine | Dnmorn | N-methylcyclo-pentylalanine | Nmcpen |
| N-methylglycine | Nala | D-N-methylphenylalanine | Dnmphe |
| N-methylamino-isobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydryoxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |

TABLE 2-continued

| Non-conventional amino acid | Code | Non-conventional amino acid | Code |
|---|---|---|---|
| L-α-ethylhistidine | Mhis | L-α-methylhomo-phenylalanine | Mhphe |
| L-α-thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenyl-alanine | Mphe | L-α-methylproline | Mpro |
| L-α-methylserine | mser | L-α-methylthreonine | Mthr |
| L-α-ethylvaline | Mtrp | L-α-methyltyrosine | Mtyr |
| L-α-methylleucine | Mval Nmbhm | L-N-methylhomo-phenylalanine | Nmphe |
| N-(N-(2,2-diphenylethyl)carbamylmethyl-glycine | Nnbhm | N-(N-(3,3-diphenylpropyl)carbamylmethyl(1)glycine | Nnbhe |
| 1-carboxy-1-(2,2-diphenylethylamino)cyclopropane | Nmbc | | |

The isolated polypeptides of present invention can be biochemically synthesized such as by using standard solid phase techniques. These methods include exclusive solid phase synthesis, partial solid phase synthesis methods, fragment condensation, classical solution synthesis. These methods are preferably used when it cannot be produced by recombinant techniques (i.e., not encoded by a nucleic acid sequence) and therefore involves different chemistry or when short peptides are synthesized.

Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques are preferably used to generate the isolated polypeptides of the present invention since these techniques are better suited for generation of relatively long polypeptides (e.g., longer than 20 amino acids) and large amounts thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

These techniques may be used to generate the polypeptide of the present invention in vitro, ex vivo and in vivo (the latter two are further described hereinbelow).

To produce an isolated HIF-1α polypeptide of the present invention using recombinant technology, an isolated polynucleotide comprising a nucleic acid sequence encoding such a polypeptide may be used. An exemplary nucleic acid sequence is set forth in SEQ ID NO: 1.

The term "nucleic acid sequence" refers to a deoxyribonucleic acid sequence composed of naturally-occurring bases, sugars and covalent internucleoside linkages (e.g., backbone) as well as oligonucleotides having non-naturally-occurring portions which function similarly to respective naturally-occurring portions. Such modifications are enabled by the present invention provided that recombinant expression is still allowed.

A nucleic acid sequence of HIF-1α according to this aspect of the present invention can be a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

In order to generate the HIF-1α polypeptides of the present invention using recombinant techniques, the polynucleotides encoding same are ligated into nucleic acid expression vectors, such that the polynucleotide sequence is under the transcriptional control of a cis-regulatory sequence (e.g., promoter sequence).

A variety of prokaryotic or eukaryotic cells can be used as host-expression systems to express the polypeptides of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

Constitutive promoters suitable for use with this embodiment of the present invention include sequences which are functional (i.e., capable of directing transcription) under most environmental conditions and most types of cells such as the cytomegalovirus (CMV) and Rous sarcoma virus (RSV).

Inducible promoters suitable for use with this embodiment of the present invention include for example the tetracycline-inducible promoter (Srour, M. A., et al., 2003. Thromb. Haemost. 90: 398-405).

The expression vector according to this embodiment of the present invention may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

Polyadenylation sequences can also be added to the expression vector in order to increase the translation efficiency of a polypeptide expressed from the expression vector of the present invention. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can also be used by the present invention. SV40 vectors include pSVT7 and pMT2. Vectors derived from bovine papillonia virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Depending on the vector and host system used for production, resultant polypeptides of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

Following production of the polypeptides of the present invention, antibodies may be generated that specifically recognize the mutant forms and not the native forms. Such antibodies may be of use for verifying expression thereof.

Since the polypeptides of the present invention comprise angiogenic effects, they may be used in the treatment a disease or condition associated with ischemia.

Thus, according to another aspect of the present invention, there is provided a method of treating a disease or condition associated with ischemia, the method comprising administering to a subject in need thereof a therapeutically effective amount of an agent capable of upregulating the polypeptides of the present invention.

As used herein the term "treating" refers to preventing, alleviating or diminishing a symptom associated with an angiogenesis-related disease. Preferably, treating cures, e.g., substantially eliminates, the symptoms associated with the angiogenesis-related disease.

As used herein the term "subject" refers to any (e.g., mammalian) subject, preferably a human subject.

As used herein, the term "hypoxia" refers to a state of reduced oxygen. This can occur when the lungs are compromised or blood flow is reduced.

As used herein, the term "ischemia" refers to a reduction in blood flow, which can be caused by the obstruction of an artery or vein by a blood clot (thrombus) or by any foreign circulating matter (embolus), or by a vascular disorder such as atherosclerosis. Alternatively, ischemia can be caused when the artery is not obstructed but target tissue demand for oxygen is increased relative to supply. Reduction in blood flow can have a sudden onset and short duration (acute ischemia), or can have a slow onset with long duration or frequent recurrence (chronic ischemia). Acute ischemia is often associated with regional, irreversible tissue necrosis (an infarct), whereas chronic ischemia is usually associated with transient hypoxic tissue injury. If the decrease in perfusion is prolonged or severe, however, chronic ischemia can also be associated with-an infarct. Infarctions commonly occur in the spleen, kidney, lungs, brain, and heart, producing disorders such as intestinal infarction, pulmonary infarction, ischemic stroke, and myocardial infarction.

The present invention thus clearly contemplates methods that can be applied to the treatment of medical conditions associated with any ischemic event, whether acute, transient or chronic. Acute ischemic events can include those associated with surgery, organ transplantation, infarction (e.g., cerebral, intestinal, myocardial, pulmonary, etc.), trauma, insult, or injury, etc. Chronic events associated with ischemia can include hypertension, diabetes, occlusive arterial disease, chronic venous insufficiency, Raynaud's disease, cirrhosis, congestive heart failure, systemic sclerosis, etc.

Other diseases or disorders associated with ischemia include but are not limited to wound healing, gastrointestinal lesions, autoimmune diseases and neurodegenerative disorders.

Examples of specific conditions include, but are not limited to, wound healing, ischemic stroke, ischemic heart disease, peripheral vascular disease, renal artery disease, gastrointestinal lesions, burns, skin transplantation, vascular grafts, organ repair (e.g., ex vivo and in vivo), bone reparative disorders, liver disorders, uterine disorders, ocular angiogenesis disorders, (i.e. retinal detachment, age related macular degeneration), bone regeneration disorders, cartilage repair disorders and smooth muscle cell disorders.

According to one embodiment, agents capable of upregulating the polypeptides of the present invention are the HIF-1α polypeptides of the present invention i.e. the polypeptides are generated and subsequently administered to a subject. Methods of generating the isolated polypeptides of the present invention are described hereinabove.

Since it is preferable that the HIF-1α polypeptides of the present invention are provided at the site of the angiogenesis (i.e. proliferating endothelial cells), preferably the polypeptides are delivered locally or comprise a targeted delivery system (e.g. targeted liposomes).

A particularly preferred method of targeting the HIF-1α polypeptides of the present invention to the site of angiogenesis is by targeted gene therapy.

Gene therapy as used herein refers to the transfer of genetic material (e.g. DNA or RNA) of interest into a host to treat or prevent a genetic or acquired disease or condition or phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ. The cells may be autologous or non-autologous to the subject. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ (Culver, 1998. (Abstract) Antisense DNA & RNA based therapeutics, February 1998, Coronado, Calif.).

These genetically altered cells have been shown to express the transfected genetic material in situ.

To confer specificity, preferably the nucleic acid constructs used to express the polypeptides of the present invention comprise endothelial cell-specific promoter sequence elements. The endothelial specific promoter element may include, for example, at least one copy of the PPE-1 promoter as set forth in SEQ ID NO: 4. Examples of suitable promoters/enhancers which can be utilized by the nucleic acid construct of the present invention include the endothelial-specific promoters: preproendothelin-1, PPE-1 promoter (Harats D, J Clin Invest. 1995 March; 95(3):1335-44)., the PPE-1-3x promoter [PCT/IL01/01059; Varda-Bloom N, Gene Ther 2001 June; 8(11):819-27], the TIE-1 (S79347, S79346) and the TIE-2 (U53603) promoters [Sato T N, Proc Natl Acad Sci USA 1993 Oct. 15; 90(20):9355-8], the Endoglin promoter [Y11653; Rius C, Blood 1998 Dec. 15; 92(12):4677-90], the von Willebrand factor [AF152417; Collins C J Proc Natl Acad Sci USA 1987 July; 84(13):4393-7], the KDR/flk-1 promoter [X89777, X89776; Ronicke V, Circ Res 1996 August; 79(2):277-85], The FLT-1 promoter [D64016 AJ224863; Morishita K, J Biol Chem 1995 Nov. 17; 270(46): 27948-53], the Egr-1 promoter [AJ245926; Sukhatme V P, Oncogene Res 1987 September-October; 1(4):343-55], the E-selectin promoter [Y12462; Collins T J Biol Chem 1991 Feb. 5; 266(4):2466-73], The endothelial adhesion molecules promoters: ICAM-1 [X84737; Horley K J EMBO J 1989 October; 8(10):2889-96], VCAM-1 [M92431; Iademarco M F, J Biol Chem 1992 Aug. 15; 267(23):16323-9], PECAM-1 [AJ313330 X96849; CD31, Newman P J, Science 1990 Mar. 9; 247(4947):1219-22], the vascular smooth-muscle-specific elements: CArG box X53154 and aortic carboxypeptidase-like protein (ACLP) promoter [AF332596; Layne M D, *Circ Res.* 2002; 90: 728-736] and Aortic Preferentially Expressed Gene-1 [Yen-Hsu Chen J. Biol. Chem., Vol. 276, Issue 50, 47658-47663, Dec. 14, 2001]. Other suitable endothelial specific promoters are well known in the art, such as, for example, the EPCR promoter (U.S. Pat. No. 6,200,751 to Gu et al) and the VEGF promoter (U.S. Pat. No. 5,916,763 to Williams et al).

Preferably, the nucleic acid constructs of the present invention further include a hypoxia response element, for example at least one copy of the sequence set forth in SEQ ID NO:5. Since HIF-1 binds to such a response element, the HIF-1α transgene expressed under the regulation of such a response element should, in turn, activate the promoter further, thus creating a positive feedback loop, enhancing the transcriptional response.

Introduction of nucleic acids by infection in both in vivo and ex vivo gene therapy offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral utilizes its natural specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art.

It will be appreciated that although adenoviruses are employed in the experiments described in examples presented hereinbelow, the constructs of the present invention could be easily adapted by those of ordinary skill in the art to other viral delivery systems.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

Since transduction of cells with conditionally replicating adenoviral vectors is significantly more effective in target cell lysis and spread of viral infection, the nucleic acid construct can include a conditionally replicating adenovirus.

The viral vectors, containing the endothelial cell specific promoters, can also be used in combination with other approaches to enhance targeting of the viral vectors. Such approaches include short peptide ligands and/or bispecific or bifunctional molecule or diabodies (Nettelbeck et al. Molecular Therapy 3:882; 2001).

The polypeptides and polynucleotides of the present invention can be provided to the individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the polypeptide or polynucleotide preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the preparation in a local rather than systemic manner, for example, via injection of the preparation directly into a specific region of a patient's body.

A recombinant vector can be administered in several ways. If vectors are used which comprise endothelial cell specific promoters, for example, the procedure can take advantage of their target specificity and consequently, do not have to be administered locally at the diseased site. Thus, according to a preferred embodiment of the present invention, the nucleic acid constructs are administered systemically (e.g. intravenously or subcutaneously). As illustrated in Example 5, systemic administration of a polynucleotide of the present invention linked to an endothelial cell specific promoter showed a much higher safety profile than systemic administration of the same polynucleotide linked to a constitutively active promoter as well as being more effective at the disease site at promoting angiogenesis.

Injection of viral vectors into a spinal fluid can also be used as a mode of administration, especially in the case of neurodegenerative diseases. Following injection, the viral vectors will circulate until they recognize host cells with appropriate target specificity for infection.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

It will be appreciated that the polypeptides and polynucleotides of the present invention can be provided to the individual with additional active agents to achieve an improved therapeutic effect as compared to treatment with each agent by itself. In such therapy, measures (e.g., dosing and selection of the complementary agent) are taken to adverse side effects which may be associated with combination therapies.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Triple Mutant HIF-1α Shows Greater Transcriptional Activity than P402A P564G and P564A N803A Double Mutants Point mutations P402A and P564G within HIF-1α were previously shown to abrogate its interaction with the tumor suppressor VHL, thus preventing its subsequent proteosomal degradation. This resulted in stabilized HIF-1α during normoxia, reaching activity levels comparable to hypoxic condition. Similarly, HIF-1α with point mutations P564A N803A was demonstrated to be as active in normoxia as wild-type HIF-1α following treatment with the hypoxia mimetic iron chelator 2,2'-dipyridyl. The present inventors hypothesized that a combination of all three mutations may result in a mutated HIF-1α, termed 'Triple mutant', which is more active than the P402A P564G mutant and more stable than the P564A N803A mutant, thus making it more potent for therapeutic angiogenesis purposes.

Materials and Methods

Cell Culture:

The following cell lines were used: Bovine aortic endothelial cells (BAECs) were a kind gift from N. Savion (Goldschleger Eye Institute, Sheba Medical Center). Human embryonic kidney cells (HEK293 cells) were purchased from American Type Culture Collection (Rockville, Md., USA). Passages 20-26 of 293 cells were used. HeLa cells were a kind gift from Y. Keisary (Tel Aviv University). Human umbilical vein ECs (HUVECs) were produced as previously described [Jaffe, E. A. et al, J Clin Invest 52, 2745-56 (1973)]. Renal cell carcinoma (RCC) cells were a kind gift from G. Lavi. (Angiogenesis Institute, Sheba Medical Center). BAEC, HEK293 cells and RCC were cultured in DMEM supplemented with 10% FCS, 2 mM glutamine and 100 U/ml penicillin/streptomycin. HeLa cells were cultured in MEM supplemented with 10% FCS and 100 U/ml penicillin/streptomycin. HUVECs were maintained in EGM-2 and 2% FCS (Clonetics. San-Diego, Calif., USA). All cells were maintained at 37° C. in a 5% $CO_2$-humidified incubator.

Expression Construct:

Wild-type HIF-1α and P564A N803A HIF-1α mutant in pEF-bos plasmids were kind gifts from M. Whitelaw (Adelaide University). P402A P564G HIF-1α mutant in pcDNA3 plasmid was a kind gift from P J. Ratcliffe (Oxford University). pCR3.1-HA-FIH-1 antisense plasmid was a kind gift from G. Semenza (Johns Hopkins University). p2.1 HRE-luciferase was purchased from American Type Culture Collection (Rockville, MD., USA) and was previously described [Mahon, P. C., et al., Genes Dev 15, 2675-86 (2001)].

Plasmid SV40-f-gal was purchased from Promega (Madison Wis., USA). Triple mutant HIF-1α was constructed by insertion of Bsu26I/NotI digested fragment of P564A N803A HIF-1α mutant into Bsu26I/NotI digested P402A P564G HIF-1α vector. The integrity of the plasmid was confirmed by DNA sequencing. For transfection experiments, wild-type and mutant HIF-1α cDNAs were subcloned into pcDNA3 vector (Invitrogen Corp., Carlsbad, Calif., USA).

Transient Transfection Experiments:

HEK 293, BAEC and RCC cells were co-transfected in triplicates in 24-well plates with 200 ng p2.1 HRE-luciferase, 100 ng pSV40-β-gal and 100 ng of either pcDNA3 empty vector, wild-type HIF-1α, P402A P564G, P564A N803A or Triple mutant using Lipofectamine Plus reagent (Invitrogen Corp., Carlsbad, Calif., USA) according to the manufacturer's instructions. For the FIH-1 antisense experiment, transfection was carried out in triplicates using Lipofectamine Plus reagent with 100 ng p2.1 HRE-luciferase, 100 ng pSV40-f-gal, 100 ng of either pcDNA3 empty vector, wild-type HIF-1α, P402A P564G, P564A N803A or Triple mutant and 0-400 ng of pcDNA3-HA-FIH-1 antisense or pcDNA3. Forty eight hours later, luciferase and j-gal activities were determined using the β-gal assay system (Promega, Madison Wis., USA) according to the manufacturer's instructions. Subsequently, luciferase was measured using a Turner Luminometer model 20e (Turner Designs, Sunnyvale, Calif., USA). Luciferase activity results were normalized for transfection efficiency using β-gal levels. For the RT-PCR experiment in HeLa, transfection of 300 ng of the various plasmids was carried out in 24-well plates with Lipofectamine Plus reagent. Magnofection of HUVEC, grown in 60 mm dishes, with plasmids was performed using Polymag (Chemicell, GmbH, Berlin, Germany) according to the manufacturer's instructions. Where indicated, treatment with 150 µM 2,2'-dipyridyl was given 16 hours prior to cell lysis.

Luciferase and β-Galactosidase Assays:

Luciferase and β-gal activities were determined using the β-gal assay system (Promega, Madison Wis., USA) according to the manufacturer's instructions. Luciferase activity results were normalized for transfection efficiency using β-gal levels.

RT-PCR Assay:

Forty eight hours post-transfection, cells were lysed and total RNA was isolated with RNeasy miniprep kit (Qiagen, Valencia, Calif.) according to the manufacturer's protocol. RNA was then reverse transcribed to cDNA using the Fast-Start PCR Master kit (Roche, Mannheim, Germany). Semi-quantitative RT-PCR was performed for the following genes: HIF-1a, GAPDH, VEGF, carbonic anhydrase 9 (CA-9) and PDGF-B. Primers, annealing temperatures and cycle numbers are detailed in Table 3 hereinbelow.

TABLE 3

| Gene | Primers and SEQ ID NOs | Annealing Temp. (° C.) | No. of Cycles |
|---|---|---|---|
| HIF-1α | Forward: GTCGGACAGCCTCACCAAACAGAG SEQ ID NO: 6 Reverse: GTTAACTTGATCCAAAGCTCTGAG SEQ ID NO: 7 | 60 | 24 |
| CA-9 | Forward: CACGTGGTTCACCTCAGCAC SEQ ID NO: 8 Reverse: CAGCGATTTCTTCCAAGCG SEQ ID NO: 9 | 60 | 30 |
| VEGF | Forward: CAGCGCAGCTACTGCCATCCAATCGAGA SEQ ID NO: 10 Reverse: GCTTGTCACATCTGCAAGTACGTTCGTTTA SEQ ID NO: 11 | 59 | 34 |
| PDGF-B | Forward: ATCGCCGAGTGCAAGACGCG SEQ ID NO: 12 Reverse: AAGCACCATTGGCCGTCCGA SEQ ID NO: 13 | 60 | 34 |

TABLE 3-continued

| Gene | Primers and SEQ ID NOs | Annealing Temp. (° C.) | No. of Cycles |
|---|---|---|---|
| GAPDH | Forward: ACCACAGTCCATGCCATCAC<br>SEQ ID NO: 14<br>Reverse: TCCACCACCCTGTTGCTGTA<br>SEQ ID NO: 15 | 60 | 24 |

Results

In both human embryonic kidney 293 (HEK293) and bovine aortic endothelial cells (BAEC), transiently transfected triple mutant HIF-1α showed a 2 to 2.5-fold increase in transcriptional activity in normoxia compared with P402A P564G and P564A N803A double mutants (FIGS. 1A-B).

Figure 1C:
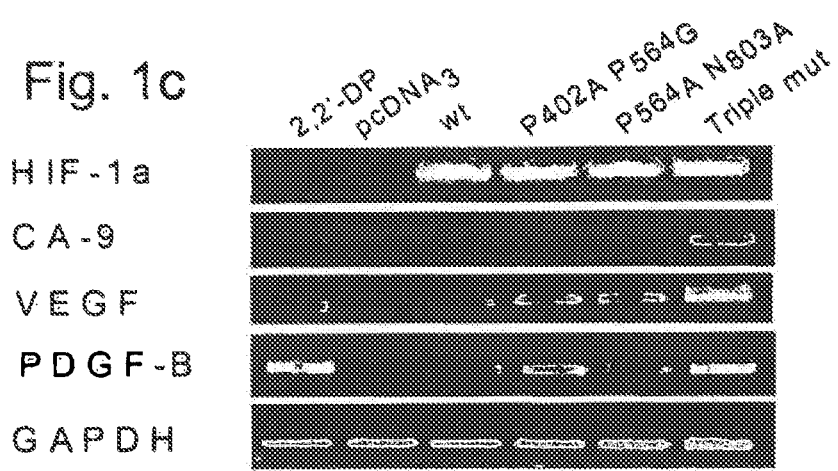
Figure 1D:
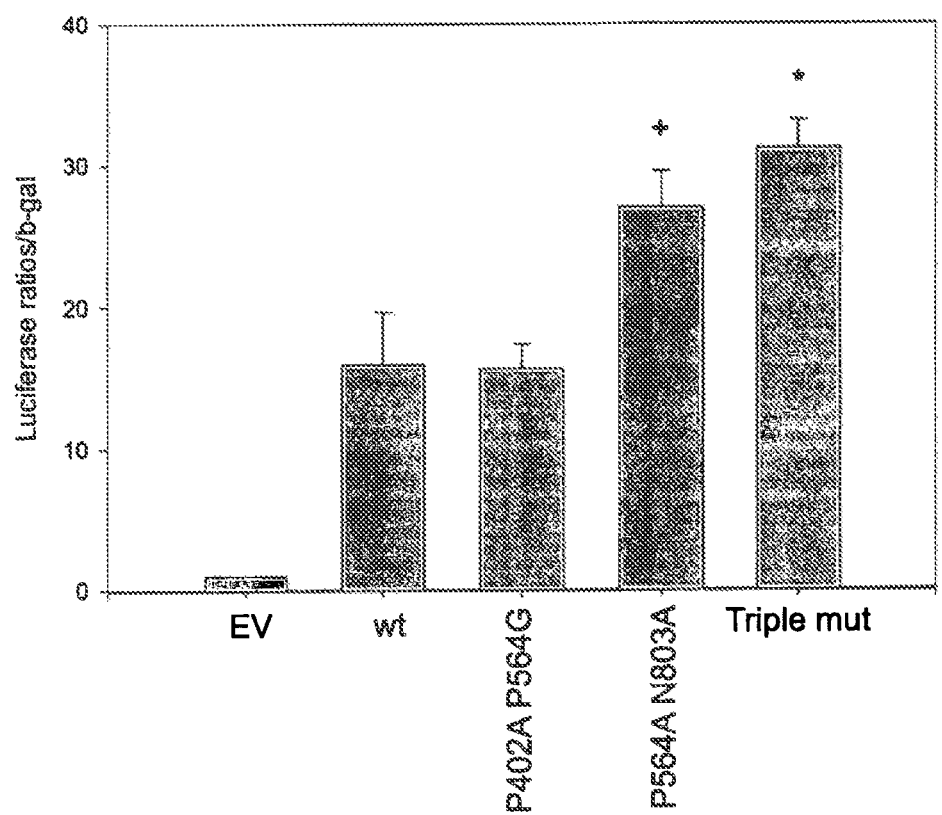

The triple mutant also led to a greater mRNA induction of HIF-1α target genes. For this, transient transfection of HeLa cells with the different mutants was followed by mRNA extraction and RT-PCR analysis. As shown in FIG. 1C, mRNA of HIF-1α in all cells transfected with HIF-1α constructs was comparable and much higher than empty vector control, as expected following transfection. In agreement with the previous results, the triple mutant HIF-1α caused greater mRNA induction of the HIF-1α target genes carbonic anhydrase 9 (CA-9), VEGF and PDGF-B than the double mutants and wild-type HIF-1a. Protein degradation of P564A N803A mutant mediated by VHL could theoretically still take place by virtue of its P402 residue which is exposed to prolyl hydroxylation. In order to prove that the observed difference in transcription induction between the triple mutant and P564A N803A mutant is due to VHL-mediated degradation, a VHL-deficient renal cell carcinoma (RCC) line was used. Assessment of HRE-mediated transcription of luciferase following transient transfection of the HIF-1α mutants in RCC in normoxia revealed an increase in activity of wild-type HIF-1α to levels of the stabilized P402A P564G mutant, indicating inhibition of proteosomal degradation (FIG. 1D). As expected, an in increase in activity of the P564A N803A mutant to the levels of the triple mutant was observed.

Figure 1E:
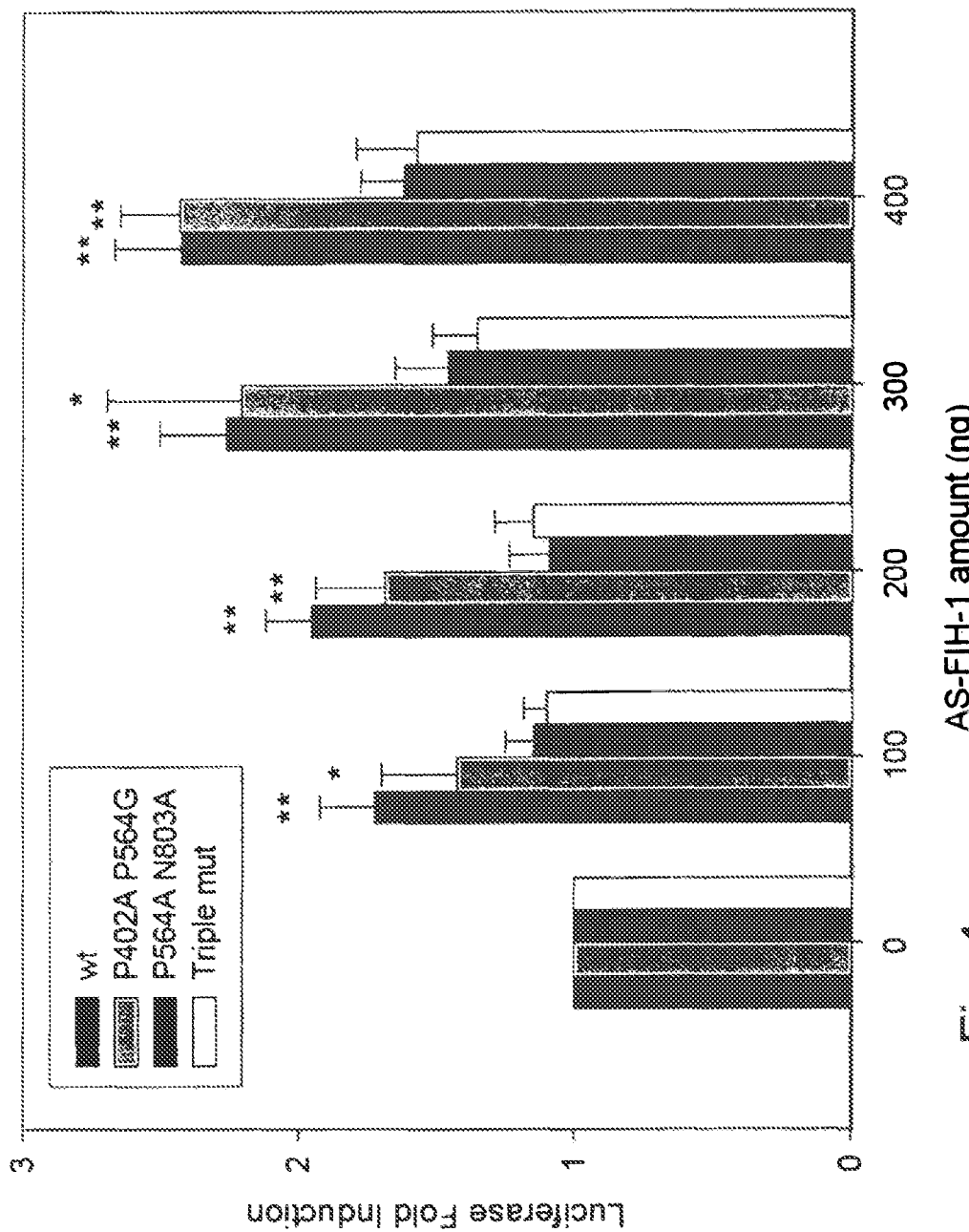

The P402A P5645G mutant, though stabilized, could theoretically still be hydroxylated at residue N803 by FIH-1, leading to its inactivation, which is the most likely explanation for the observed difference in transcription between it and the triple mutant. Inhibition of FIH-1 by antisense knockout treatment in HEK293 resulted in a dose-dependent increase of HRE-mediated transcription by wild-type HIF-1α in normoxia [FIG. 1E]. As expected, FIH-1 inhibition caused a greater fold-induction of P402A P564G mutant activity than of the Triple mutant, indicating that FIH-1 is indeed at least partly responsible for the previously observed higher activity of the triple mutant.

Example 2

Activation of C-Transactivation Domain is Essential for Optimal HIF-1α-Mediated Angiogenesis In order to assess the significance of the triple mutant's increased transcription ability in terms of therapeutic angiogenesis, a comparison of the different mutants was carried out using an in-vitro angiogenesis assay following transfection of the HIF-1α constructs in human umbilical vein endothelial cells (HUVEC).

Materials and Methods

In-Vitro Angiogenesis Assay:

Transfected or infected HUVECs, grown in 60 mm dishes, were maintained for 24 hours in EGM-2 medium followed by medium replacement with EBM-2. Cells were maintained in EBM-2 for further 24 hours, prior to assay. Cells were then trypsinized and seeded at concentration of 50,000 cells per well on 24-well plate pre-coated with growth factor reduced matrigel (BD Biosciences, USA). Capillary and tube formation was tracked for 8 hours. Quantitation of capillary formation was performed by counting the number of capillary branches per high power microscopic field in 5 random microscopic fields.

VEGF ELISA:

Transfected or infected HUVECs, grown in 60 mm dishes, were maintained for 24 hours in EGM-2 medium followed by medium replacement with EBM-2. Cells were maintained in EBM-2 for a further 24 hours, prior to addition of lysis buffer (20 mM Tris pH 7.5 in PBS, 1% Triton with complete mini protease inhibitor cocktail tablet, Roche Diagnostics, GmBH, Germany). Cell lysates were centrifuged at 10,000 rpm for 15 minutes. ELISA for human VEGF protein was performed according to the manufacturer's protocol (R& D Systems).

Western Blot Analysis:

HUVECs were cultured in 60-mm dishes and grown to subconfluence. Cells were infected with Ad-PPE-Triple, Ad-CMV-Triple, Ad-CMV-wt or Ad-CMV-GFP as described above. After lysis and evaluation of protein content (Micro BCA; Pierce Biotechnology Inc., Rockford, Ill., USA), samples containing equal amounts of protein were separated by SDS-PAGE and transferred to Optitran BA-S83 reinforced nitrocellulose membranes (Schleicher & Schuell BioScience Inc., Keene, N.H., USA). The membranes were probed with mouse anti-human HIF-1α polyclonal antibody (Santa Cruz Biotechnology Inc., Santa Cruz, Calif., USA), followed by HRP-conjugated secondary antibodies and ECL reaction.

Results

While the empty vector caused no tube formation, all HIF-1α constructs, VEGF and FCS positive controls stimulated angiogenesis (FIGS. 2A-F). Wild-type HIF-1α and P402A P564G stimulated tube formation to a similar extent but both had a significantly reduced angiogenic effect compared to P564A N803A and the triple mutant (p<0.001) (FIG. 2G). In agreement with these findings, the VEGF protein concentration in HUVECs following treatment with wt-HIF1α or P402A P564G was very similar and significantly lower than treatments with P564A N803A or Triple mutant (p=0.029) (FIG. 2H). Treatment with the P564A N803A or Triple mutant resulted in a 6-fold and 10-fold increase in VEOF protein respectively, compared with wt-HIF1α and P402A P564G (FIG. 2H). These results indicate that stability of HIF-1α is insufficient and that a constitutively active C-TAD is essential for maximal angiogenic effect of HIF-1α. No difference was observed between P564A N803A and the triple mutant. This may be due to high HIF-1α overexpression which had saturated the hydroxylase enzymes, thus masking any differences which are due to stability, similar to the state found within the RCC in FIG. 1D.

Example 3

Expression and Specificity of the PPE-1-3x Promoter in Ischemia

A prerequisite for the feasibility and safety of systemic pro-angiogenic gene therapy is the sufficiently robust and specific expression within the target ischemic tissue. In order to characterize the expression and specificity of a modified PPE-1 promoter in the setting of ischemia, an adenovirus expressing GFP under the regulation of PPE-1-3x was used (Ad-PPE-1-3x-GFP).

Materials and Methods
Construction of Adenoviral Vectors:
Ad-PPE-Triple, Ad-CMV-Triple, and Ad-CMV-wt vectors were generated by homologous recombination by Vector Biolabs (Philadelphia, USA). Successful creation of viral constructs was verified by PCR, following which two rounds of plaque purification were performed. Viral plaques subsequently underwent large-scale amplification in HEK293, followed by CsCl purification.

Animals:
Twelve-week old female C57BL/6J mice (Harlan Laboratories Ltd., Jerusalem. Israel) were used. All animal procedures were approved by the Animal Care and Use Committee of Sheba Medical Center.

Hindlimb Ischemia Model and Adenovirus Injections:
Twelve-week old C57BL/6J female mice were anesthetized using a mixture of ketamine and xylazine. They were subjected to hindlimb ischemia by a modification to the procedure described by Couffinhal et al. [15]. The skin overlying the left femoral artery was incised, followed by ligations of the femoral artery proximal to the bifurcation of the deep and superficial femoral arteries, and proximal to the popliteal artery. The portion of the artery between the ligatures was then removed and all side branches were excised. For local intramuscular injections, 20 µl of $2\times10^{10}$ VP or saline were injected at time of surgery at each of three sites: quadriceps femoris, adductor and gastrocnemius muscles. For systemic intravenous injections, 100 µl of $1\times10^{11}$ VP or saline were injected via the tail vein 7 days post-surgery.

GFP Analysis:
Mice were sacrificed 7 days after virus injection, and gastrocnemius muscle tissues were collected and fixed in 4% paraformaldehyde in 0.1 M phosphate buffer at 4° C. for 24 hours, soaked in 30% sucrose solution at 4° C. for 48 hours and then frozen in OCT compound (Sakura, Calif., USA). Tissue blocks were sliced by a cryomicrotome into 5 µm-thick transverse sections and observed directly under a fluorescent microscope (FITC filter). All tissue processing was performed under dim light to prevent GFP bleaching.

Results
Mice were subjected to hindlimb ischemia by ligation of the femoral artery or to sham procedure, followed by intramuscular injection of Ad-PPE-1-3x-GFP. Control animals were injected with Ad-CMV-GFP or saline. Expression of GFP following Ad-CMV-GFP injection was detected in muscle histological sections in both myocytes and endothelial cells of ischemic and non-ischemic muscles. In contrast, GFP expression following Ad-PPE-1-3x-GFP injection was detected in endothelial cells of ischemic muscles while no expression was identified in non-ischemic muscle. These results demonstrate the specificity to endothelium and to ischemic condition of the modified PPE-1 promoter.

Intravenous delivery of Ad-PPE-1-3x-GFP was effected in order to determine whether this promoter could also lead to expression following intravenous systemic injection, where the virus is disseminated in the body and only a small fraction of it reaches the target organ. For this end, mice subjected to hindlimb ischemia or to sham procedure were injected 7 days post-surgery via the tail vein with Ad-PPE-1-3x-GFP and Ad-CMV-GFP or saline as controls. Since immediately following femoral artery ligation the blood flow in the ischemic hindlimb falls to less than 10% of the normal limb and is almost absent in our model, there was a waiting interval of 7 days prior to injection, with the aim of enabling sufficient vascularisation to develop, thus allowing the virus to reach its ischemic target. As shown in FIGS. 3A-F, whereas non-specific expression of GFP was detected in histological sections of both ischemic and non-ischemic muscles following systemic injection of Ad-CMV-GFP (FIGS. 3B and 3E), specific expression of GFP only in endothelial cells of ischemic muscle was noted following injection of Ad-PPE-1-3x-GFP (FIGS. 3C and 3F).

Example 4

Local Injection of Ad-PPE-Triple HIF-1α Augments Ischemic Neovascularization

The following experiments were performed in order to determine whether intramuscular treatment with adenoviral-mediated triple mutant HIF-1α under the expression of PPE-1-3x promoter could promote angiogenesis in-vivo.

Materials and Methods
Monitoring of Hindlimb Blood Flow:
Mice were anesthetized and placed for 5 minutes on a heating plate at 37° C. in order to minimize temperature variation. Hindlimb blood flow was measured with a laser Doppler perfusion imager system (Moor Instruments Ltd., UK) immediately after surgery and at days 7, 14, 21 and 28 post-surgery. Low and/or no perfusion signal was displayed in blue, whereas the highest perfusion signal was displayed in red. Color photographs were recorded and analyses were performed by calculating the average perfusion of the ischemic and non-ischemic hindlimb. To account for variables such as ambient light and temperature, the results are expressed as ratio of perfusion in the left (ischemic) vs. right (non-ischemic) hindlimb.

Immunohistochemistry and Quantification of Capillary Density:
Upon sacrifice at day 28, hindlimb muscle tissues were excised and frozen in Tissue-Tek OCT compound (Sakura Finetek USA Inc., Torrance, Calif., USA) and cryosectioned transversely. ECs were immunostained using rat monoclonal anti-CD31 antibodies (Pharmingen, San Diego, Calif., USA). The background was stained with hematoxylin.

Figure 4A:
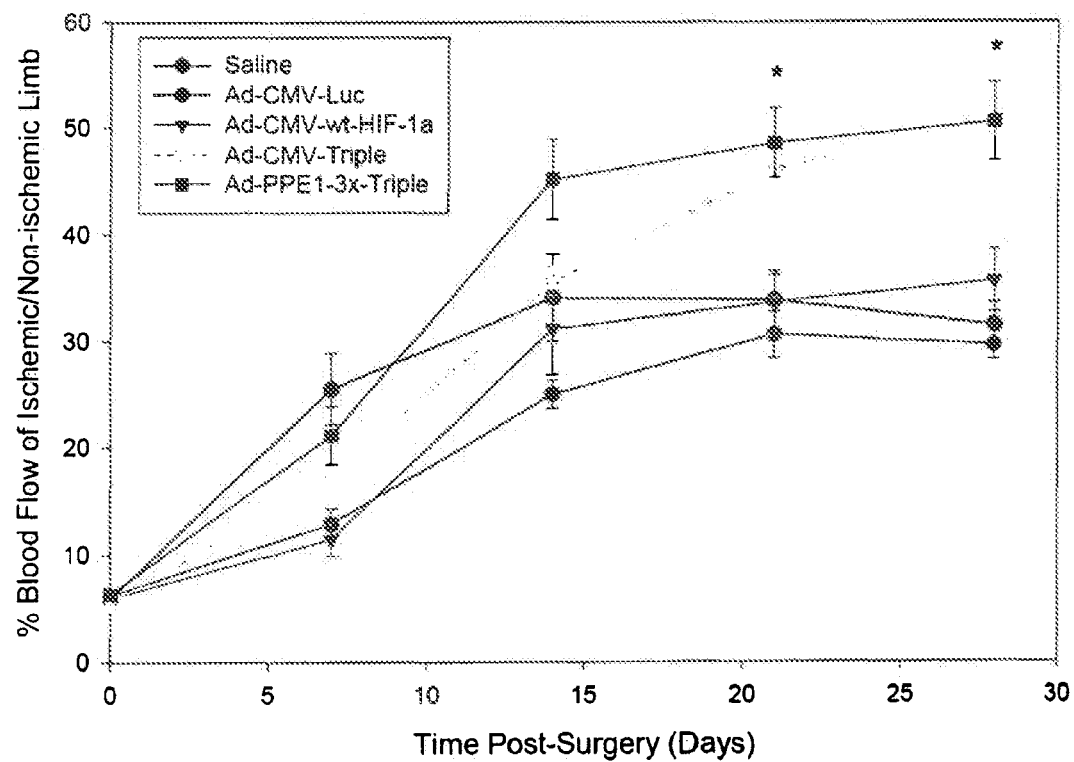
FIGS. 4A-F illustrate Post-ischemic angiogenesis is augmented by local Ad-CMV-Triple and Ad-PPE-Triple treatments.
Figure 4B:
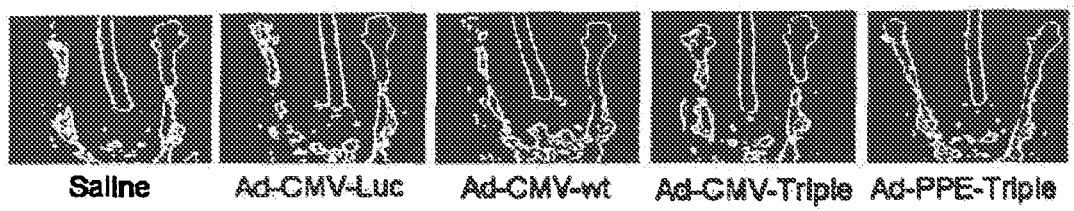
Figure 4C:
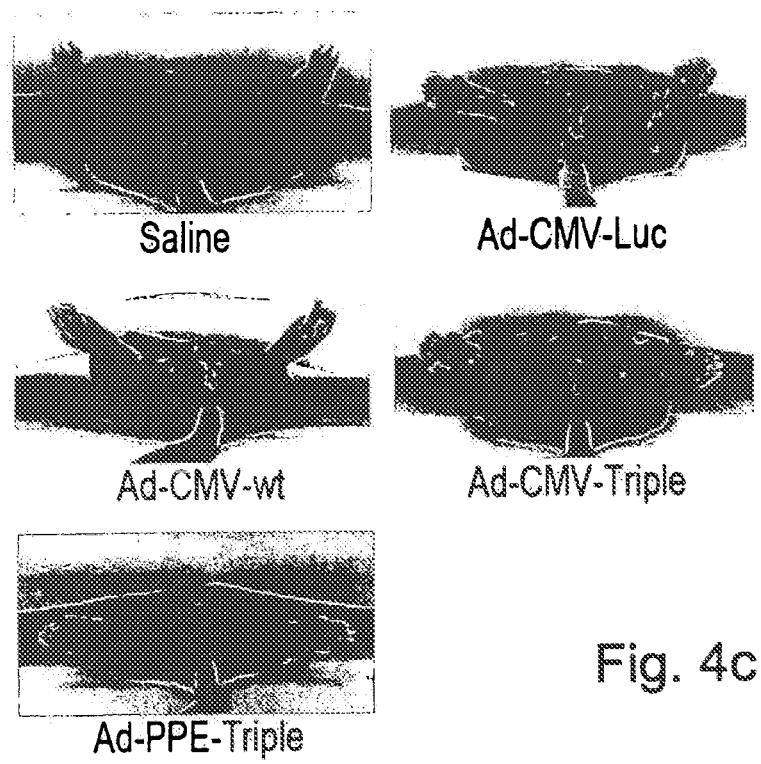
Figure 4D:
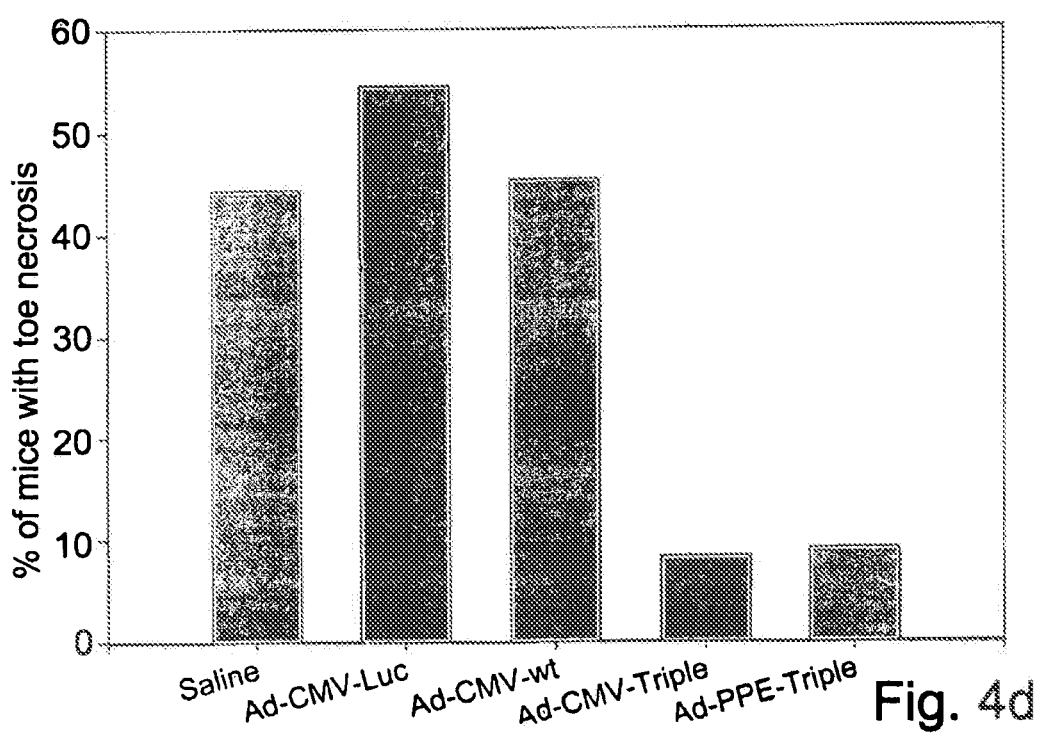
Figure 4E:
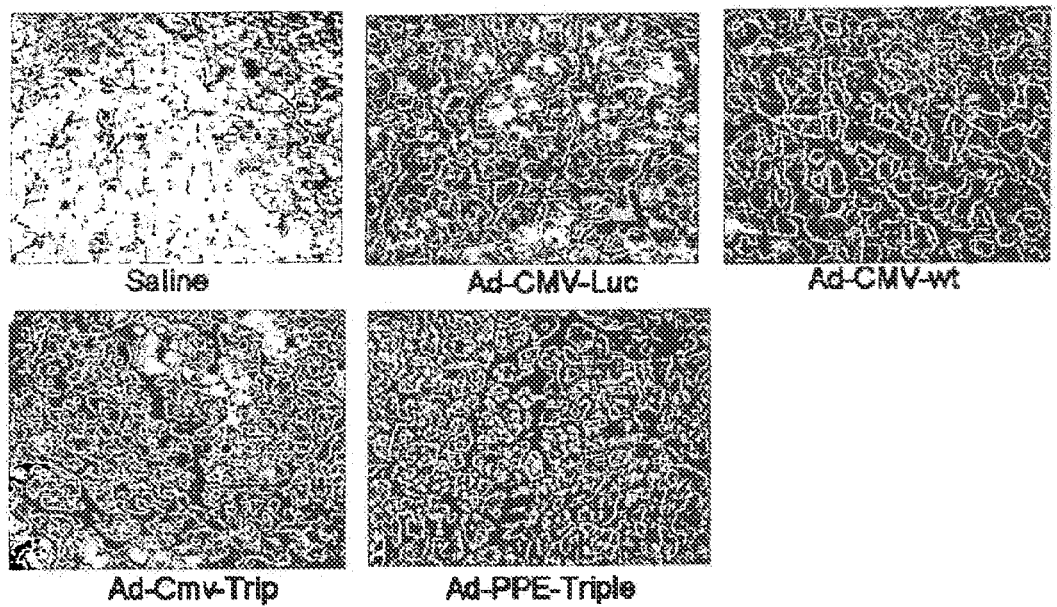
Figure 4F:
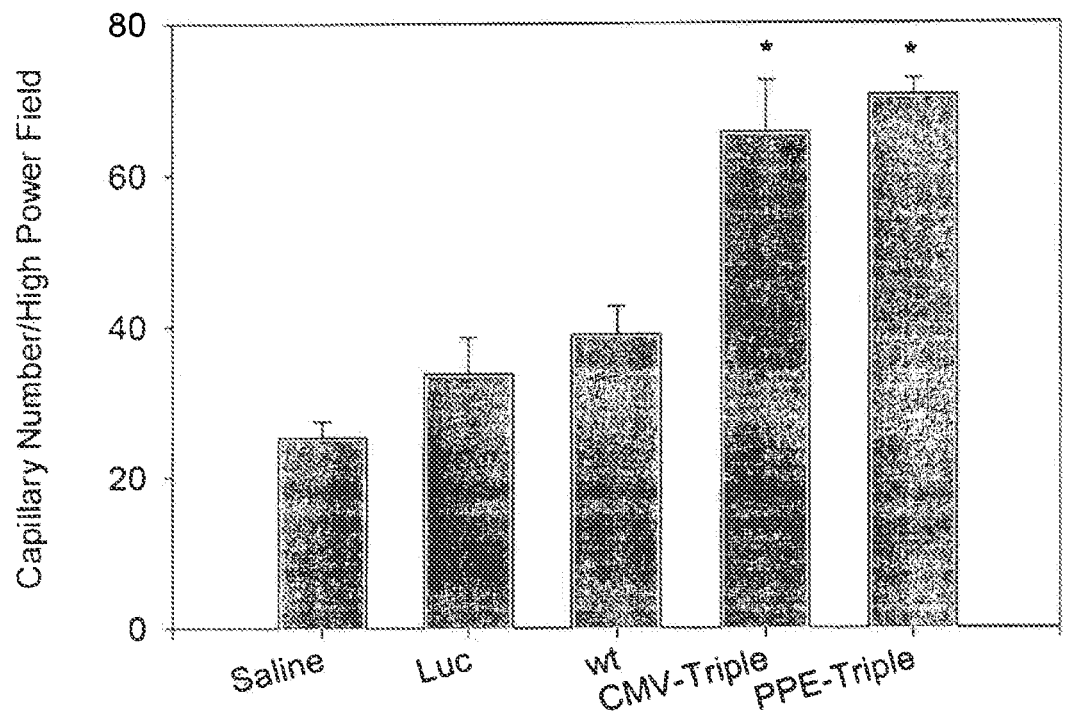

Results
Hindlimb ischemia was induced in mice followed by intramuscular injection of Ad-PPE-1-3x-Triple, Ad-CMV-Triple or Ad-CMV-wt. Control animals were injected with Ad-CMV-Luc or saline. Blood flow, clinical outcome and indices of angiogenesis were examined over a period of 28 days. Immediately following surgery, blood flow in the ischemic limb fell to less than 10% of the normal limb in all mice groups. By day 21, mice treated with Ad-CMV-Triple or Ad-PPE-1-3x-Triple showed significantly increased hindlimb blood flow relative to mice treated with Ad-CMV-wt, Ad-CMV-Luc or saline controls (FIG. 4A). By day 28, both Ad-CMV-Triple and Ad-PPE1-3x-Triple improved perfusion in the ischemic limb to approximately 50% of the normal limb, significantly more than Ad-CMV-wt or control treatments (FIGS. 4A-B). Moreover, treatment with Ad-CMV-Triple or Ad-PPE-Triple managed to profoundly reduce ischemia-induced toe necrosis and autoamputation, which were prominent in the mice treated with Ad-CMV-wt or controls, consistent with improved blood flow to the ischemic limb (FIGS. 4C-D). In agreement with the blood flow findings, quantification of muscle capillary density following CD31 staining revealed higher capillary to muscle fiber ratio in the animals treated with Ad-CMV-Triple and Ad-PPE-1-3x-Triple than Ad-CMV-wt and control-treated animals (FIGS. 4E and 4F).

Example 5

Systemic Administration of Ad-PPE-1-3x-Triple is Safer and Shows No Side-Effects Compared with Ad-CMV-Triple The following experiments were performed to compare the safety profile of systemic administration of Ad-PPE-1-3x-Triple to that of Ad-CMV-Triple. In contrast to local intramuscular injection where most of the adenovirus is concentrated at the site of injection, following intravenous administration via the tail vein most of the adenovirus reaches and transduces the liver. Therefore, with regards to safety of the treatment, it was especially important to monitor any changes in liver function and other systemic manifestations occurring in the mice.

Materials and Methods

Measurement of Serum Bilirubin, AST and ALT:

Mice sera were obtained at day 5 and 21 post-injection and analyzed using an automatic analyzer.

Immunohistochemistry and Quantification of Capillary Density:

as described in Example 4.

Monitoring of Hindlimb Blood Flow:

as described in Example 4.

Statistical Methods:

SigmaStat (SPSS Science, Chicago, Ill., USA) was used for statistical analysis. One-way repeated-measures ANOVA was performed in the in vitro studies, and Student's t test was used for the hindlimb ischemia model; P less than 0.05 was considered significant. Data are presented as mean±SEM and were graphed using SigmaPlot or Microsoft Excel (Microsoft Corp., Redmond, Wash., USA).

Results

Figure 5A:
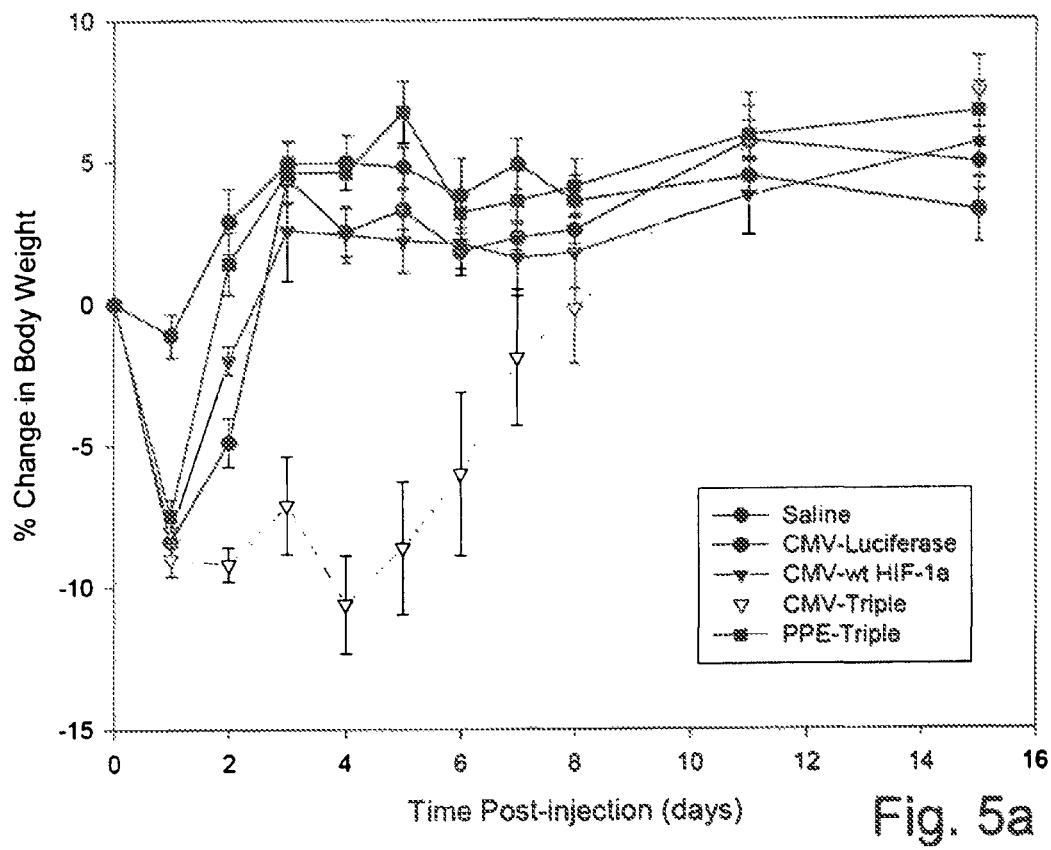
Figure 5B:
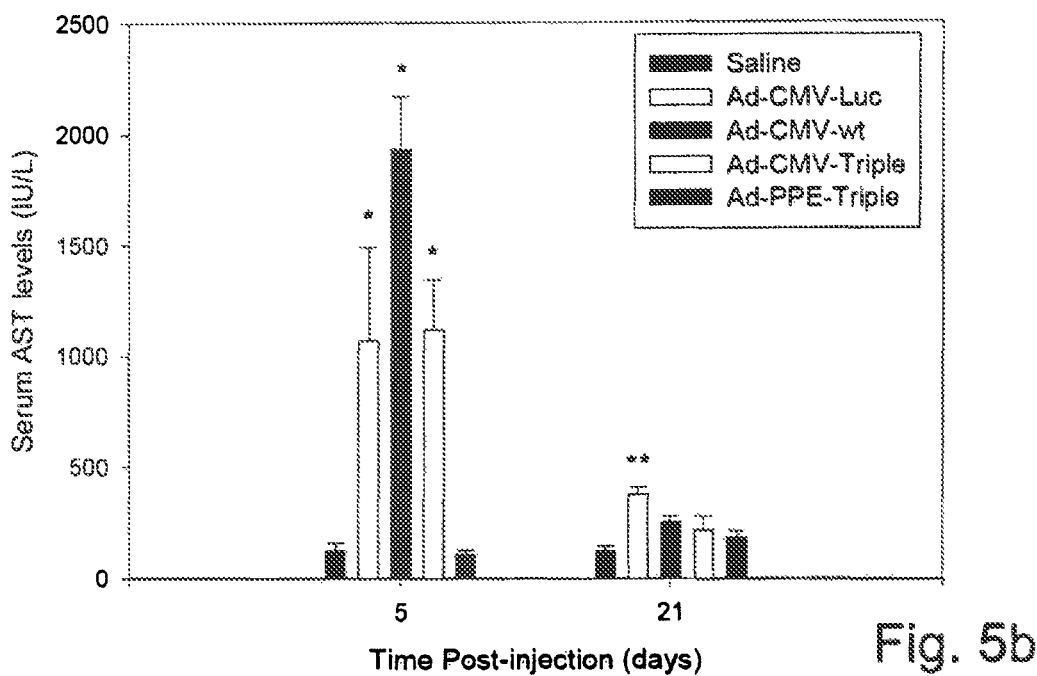
FIGS. 5B-D are bar graphs illustrating Serum bilirubin (FIG. 5B), AST (FIG. 5C) and ALT (FIG. 5D) levels at 5 and 21 days following systemic injection of saline or adenovirus.
Figure 5C:
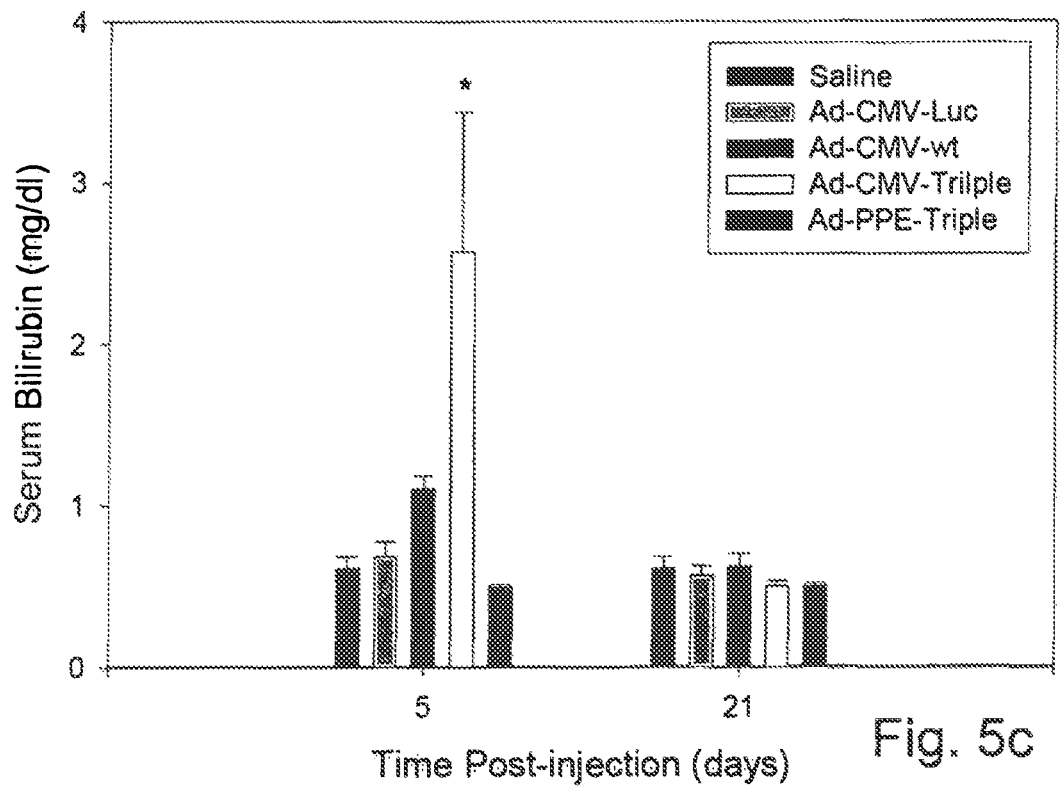
Figure 5D:
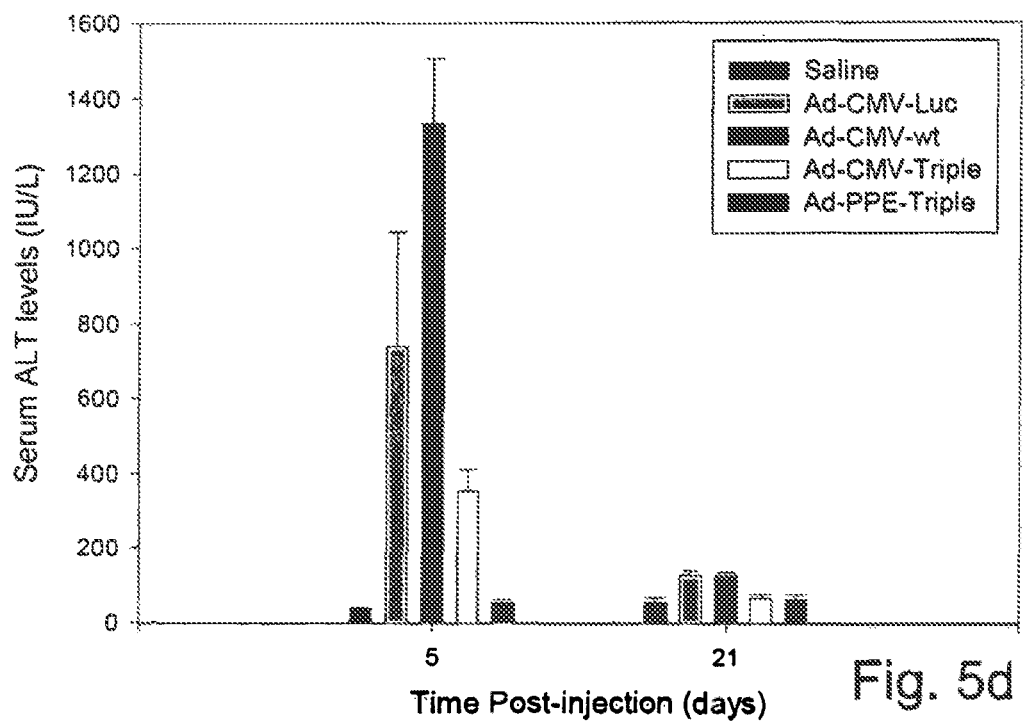

Mice subjected to hindlimb ischemia were injected systemically via the tail vein 7 days post-surgery with Ad-PPE-1-3x-Triple, Ad-CMV-Triple and Ad-CMV-wt, while Ad-CMV-Luc and saline served as controls. One day following injection, all groups of mice but the saline-treated showed a marked reduction in body weight. However, whereas all other adenovirus-treated mice regained their original body weight by day 3 post-injection, the Ad-CMV-Triple treated mice continued to decrease in weight reaching a peak 10% reduction by day 4, indicating systemic illness (FIG. 5A). Liver function tests of the mice were performed 5 days post-injection and revealed a marked 25-fold serum bilirubin increase in the Ad-CMV-Triple treated mice over saline control, demonstrating severe jaundice. Ad-CMV-wt caused a milder serum bilirubin increase (FIG. 5C). Furthermore, serum AST and ALT levels were profoundly elevated by day 5 in mice treated with Ad-CMV-Triple, Ad-CMV-wt and also Ad-CMV-Luc (FIGS. 5B and 5D). In contrast to the overt systemic manifestations of hepatic illness exhibited by the Ad-CMV-Triple treated mice, the mice treated with Ad-PPE-Triple showed no signs of illness and had their serum bilirubin, AST and ALT levels comparable to saline-treated mice. In accordance with these findings, liver histological sections of mice sacrificed at day 5 revealed remarkable inflammation and lymphocytic infiltration in the Ad-CMV-Triple treated mice while Ad-PPE-1-3x-Triple, Ad-CMV-Luc and saline controls showed no pathology (FIGS. 5E-N). Mild lymphocytic infiltration was also noted in the Ad-CMV-wt treated group. Following this acute phase of hepatic pathology, the Ad-CMV-Triple treated mice showed gradual partial recovery. They regained their weight, and by day 28 post-injection their serum bilirubin had returned to normal. However, their serum AST and ALT were still elevated compared with Ad-PPE-1-3x-Triple and saline control treated mice, similarly to Ad-CMV-wt and Ad-CMV-Luc groups. This partial liver recovery was seen also in liver histological sections from day 21 post-injection (FIG. 5E-N), showing mild residual lymphocytic infiltration in the animals treated with Ad-CMV-triple.

Figure 6A:
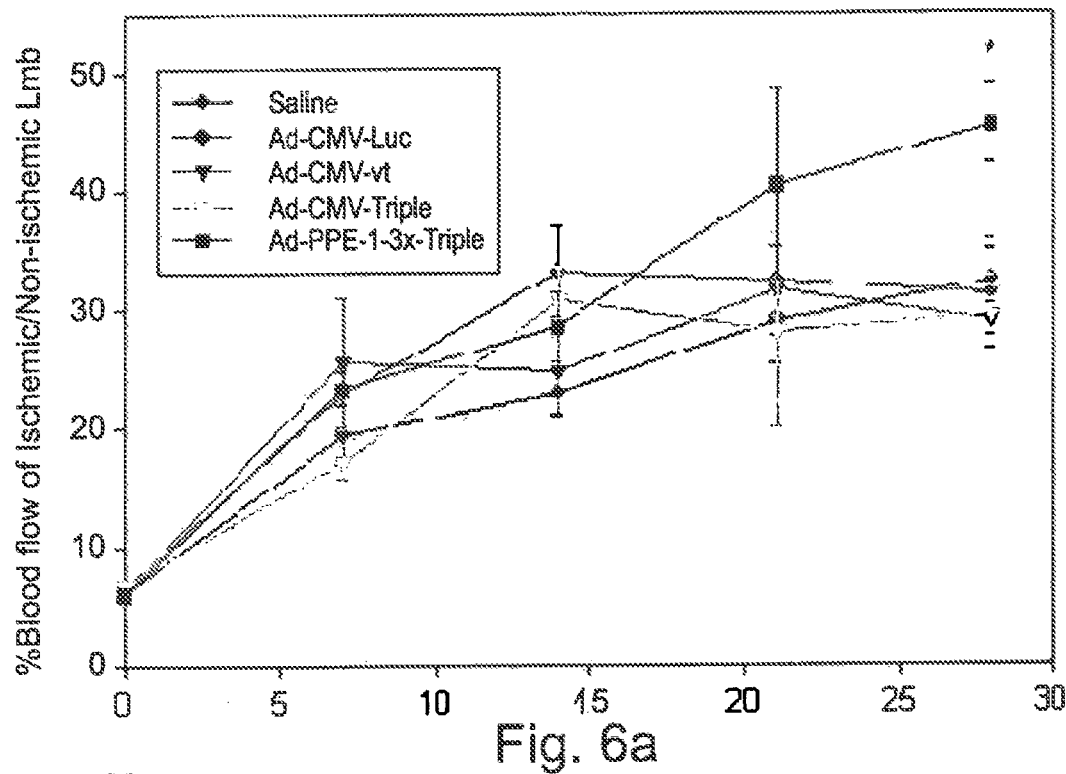
FIGS. 6A-F illustrate that post-ischemic angiogenesis is augmented by systemic Ad-PPE-Triple but not by Ad-CMV-Triple treatment.
Figure 6B:
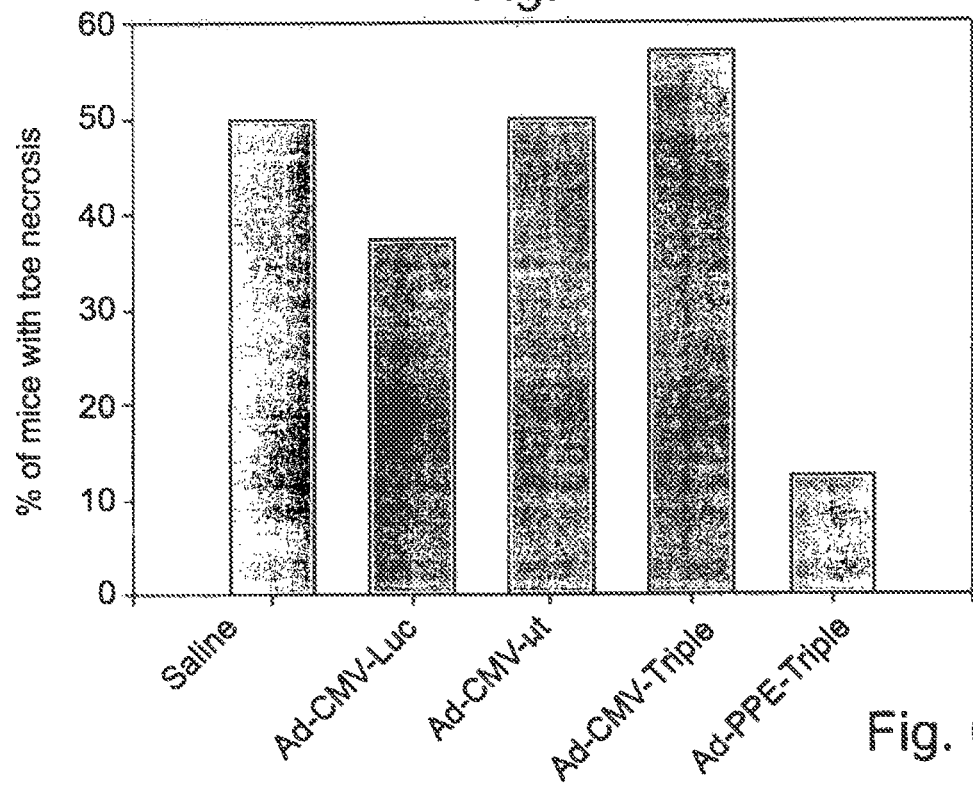
Figure 6C:
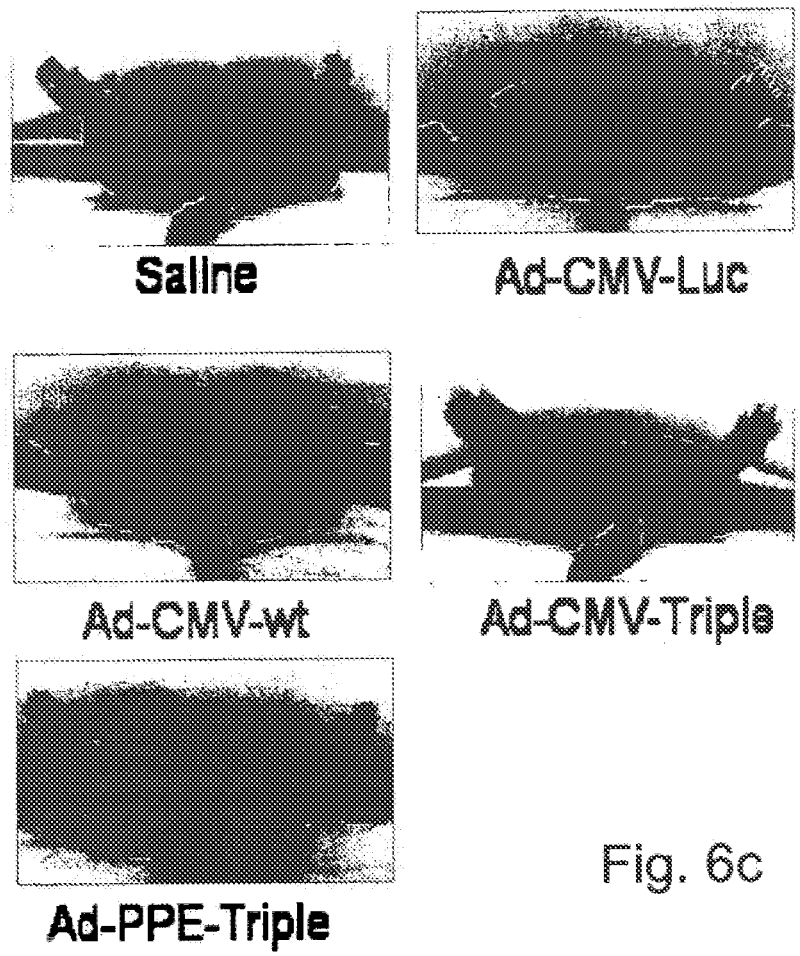
Figure 6D:
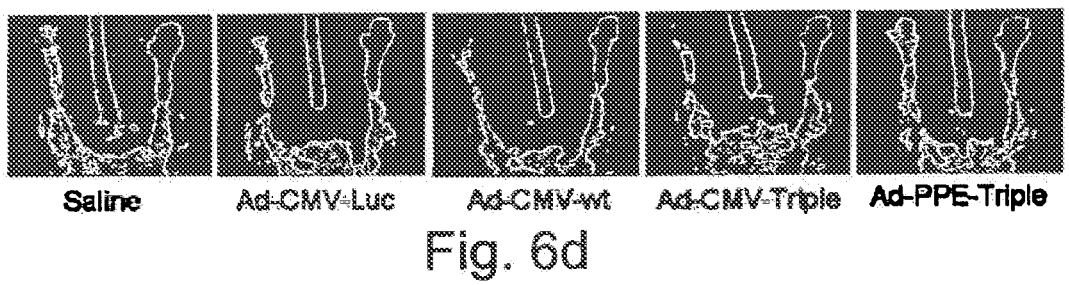
Figure 6E:
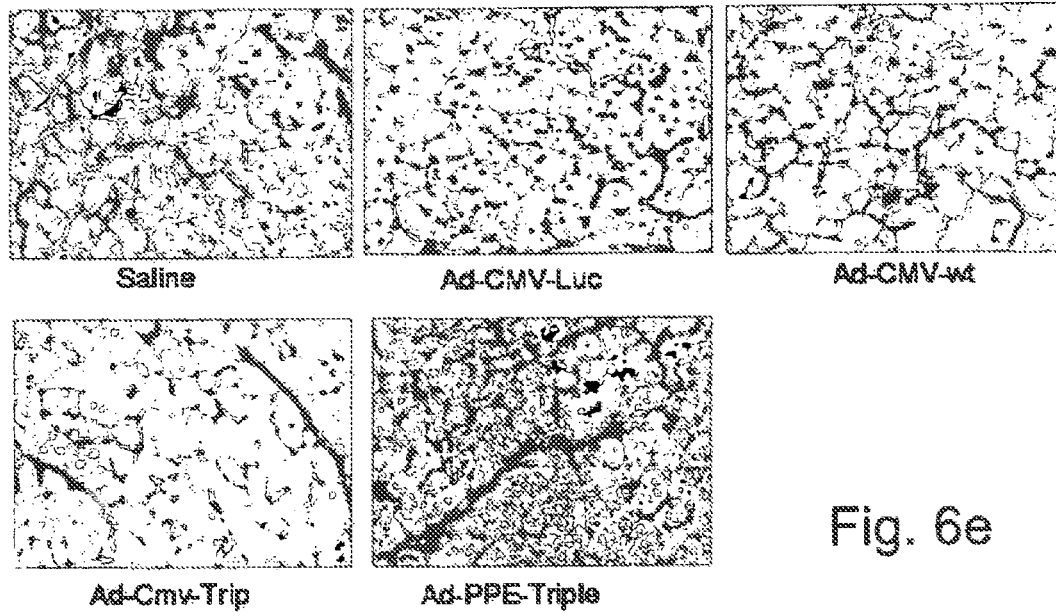
Figure 6F:
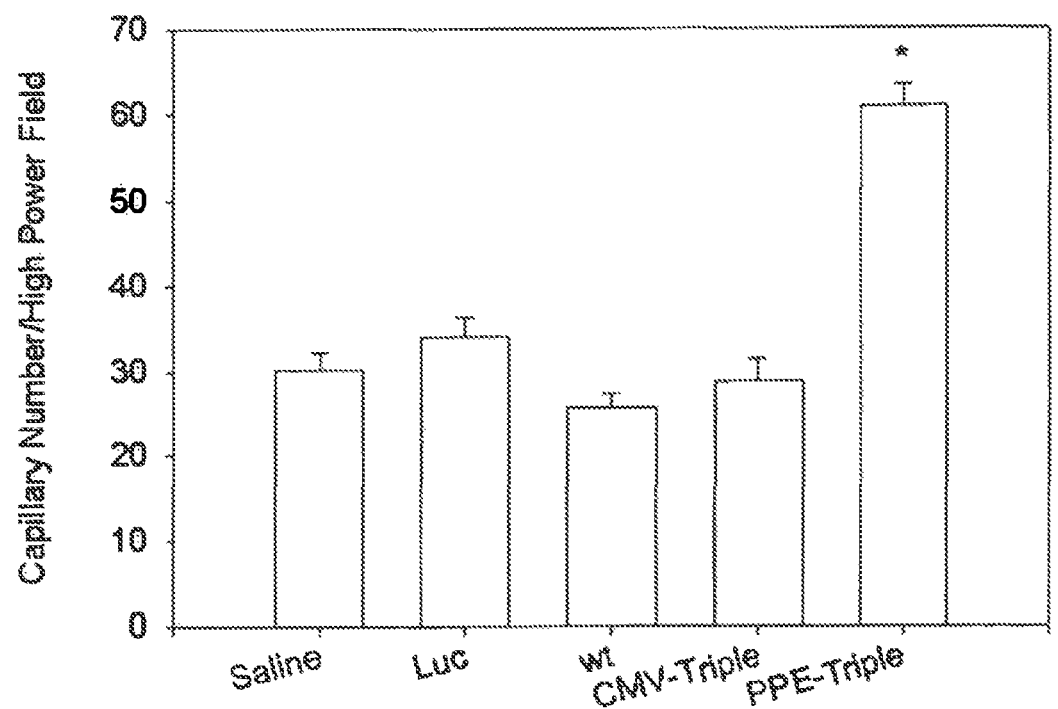
Figure 7A:
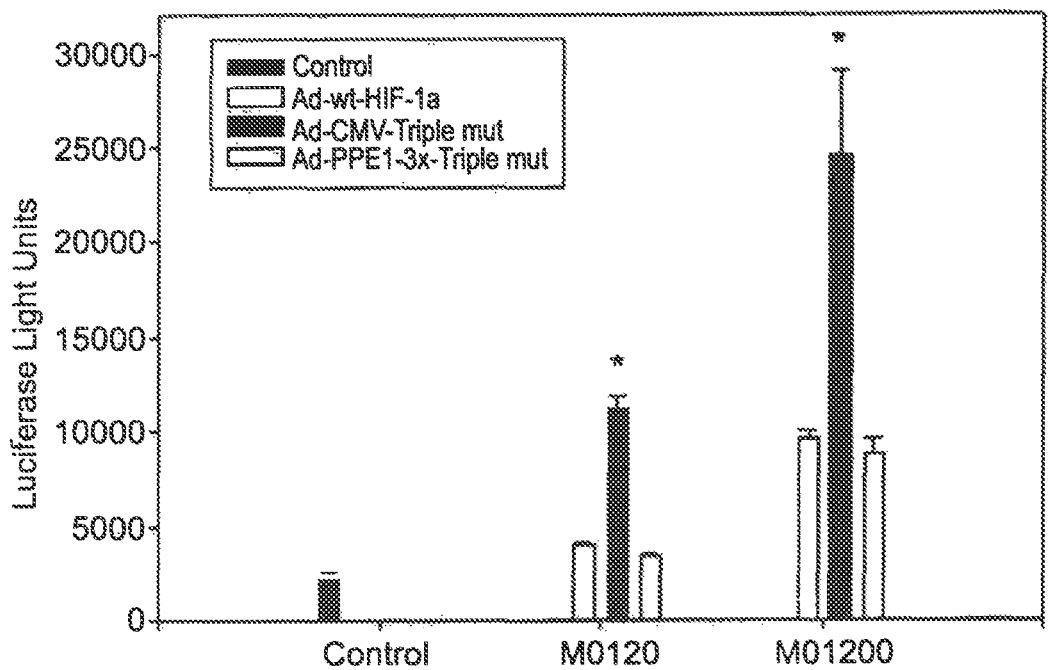
FIG. 7A is a comparison of HRE-mediated transcription of HIF-1α expressing adenoviruses in BAEC. BAEC were transfected with p2.1 HRE-Luc, followed 24 h later by infection with adenoviruses at MOI 20 or MO 200. Data are expressed as luciferase light units (mean±S.D).
Figure 7B:
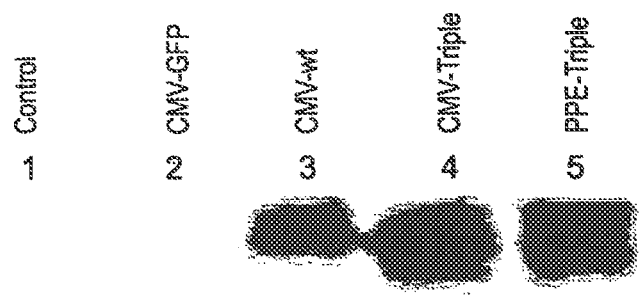
FIG. 7B is a Western blot of HIF-1α in HeLa cells. Infection of HeLa cells with Ad-CMV-GFP, AD-CMV-wtHIF-1α, Ad-CMV-Triple or Ad-PPE1-3x-Triple, or mock infection were carried out. Western blot was performed 48 h following infection.
Figure 7C:
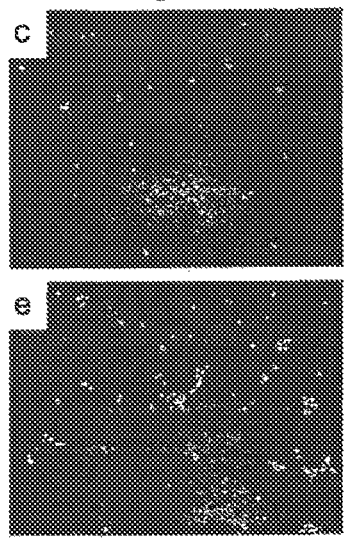
FIGS. 7C-G: In-vitro angiogenesis assay for HIF-1α expressing adenoviruses in HUVEC. HUVEC were either mock infected (C), infected with Ad-CMV-GFP (D), Ad-CMV-wtHIF-1α (E), Ad-CMV-Triple (F) or Ad-PPE1-3x-Triple (0). Forty eight hours later, in-vitro angiogenesis assay was performed. Figures C-G are representative photographs of tube formation.
Figure 7D:
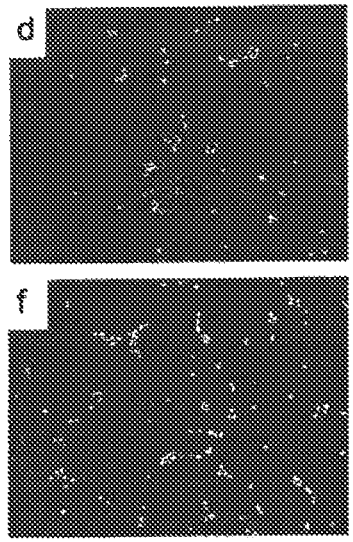
Figure 7E:
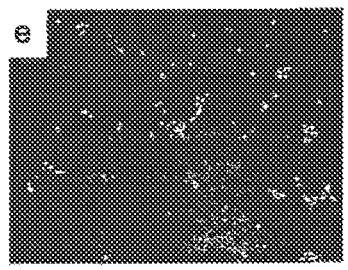
Figure 7F:
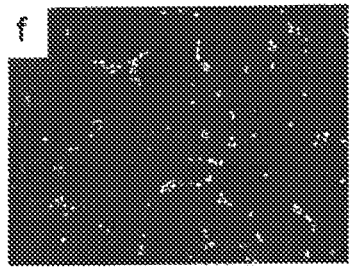
Figure 7G:
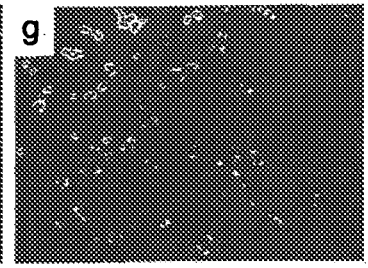
Figure 7H:
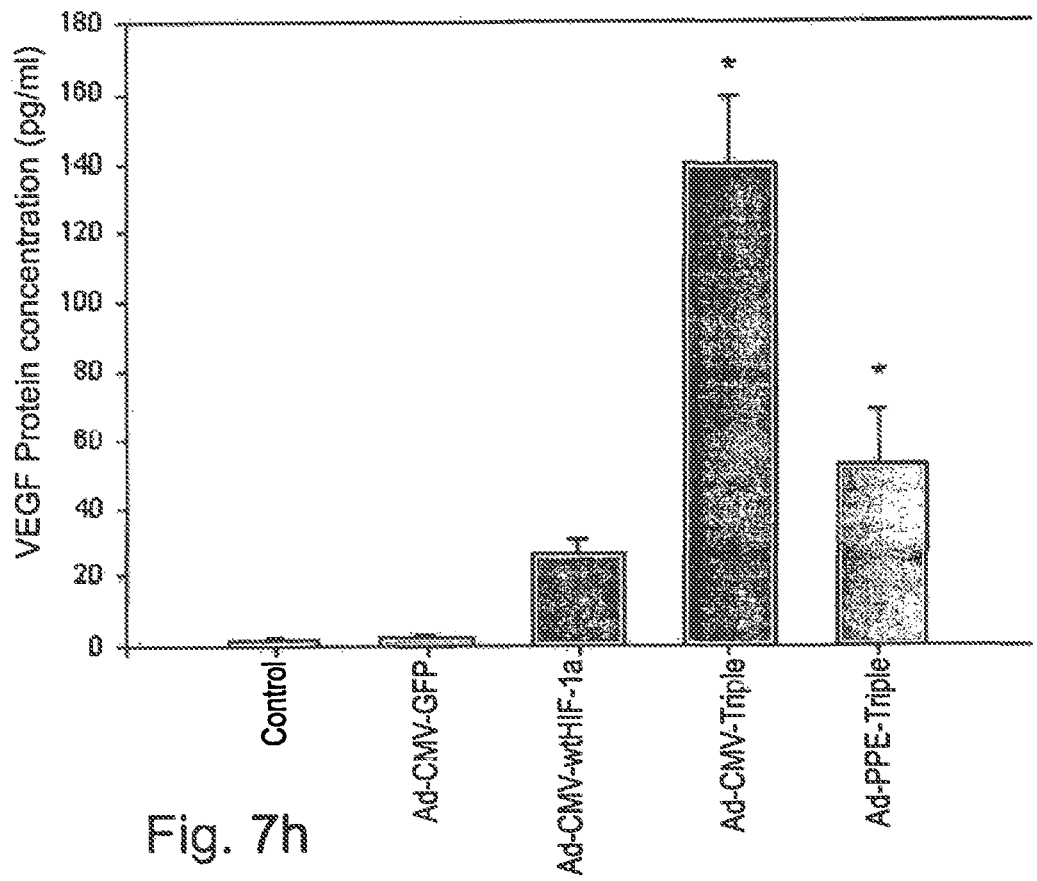
FIG. 7H: is a bar graph illustrating VEGF protein concentration of infected HUVECs, as determined by ELISA and results are expressed as mean±S.D. *p=0.01 vs. Ad-CMV-wtHIF-1α.

Following treatment, mice treated with Ad-PPE-Triple demonstrated a significantly greater improvement in blood perfusion in the ischemic hindlimb compared with Ad-CMV-Triple and all other treatment groups, which was first noted on day 21 post-surgery, reaching approximately 45% perfusion of the normal limb by day 28 post-surgery vs. 30% in the Ad-CMV-Triple group (FIGS. 6A-B). The clinical outcome of the ischemic hindlimb was consistent with the increased blood flow, demonstrating a marked reduction in toe necrosis and autoamputation in the Ad-PPE-Triple mice vs. all other groups (FIGS. 6C-D). In addition, quantification of muscle capillary density following CD31 staining showed higher capillary to muscle fiber ratio in the group treated with Ad-PPE-1-3x-Triple than the Ad-CMV-Triple and all other groups (FIGS. 6E-F).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An endothelial cell-specific promoter comprising the sequence as set forth in SEQ ID NO: 4.

2. The endothelial cell-specific promoter of claim 1, wherein the promoter is operably linked to a gene encoding a polypeptide.

3. A recombinant polynucleotide comprising the endothelial cell-specific promoter of claim 1 operably linked to a nucleotide sequence encoding a polypeptide.

4. The polynucleotide of claim 3, wherein the polypeptide has HIF-1α activity.

5. The polynucleotide of claim 4, wherein the polypeptide comprises an amino acid sequence at least 90% identical to SEQ ID NO: 3.

6. The polynucleotide of claim 4, wherein the polypeptide comprises SEQ ID NO: 3 with a mutation at a position corresponding to proline 402 of SEQ ID NO: 3, a mutation at a position corresponding to proline 564 of SEQ ID NO: 3, or a mutation at a position corresponding to asparagine 803 of SEQ ID NO: 3.

7. The polynucleotide of claim 6, wherein the polypeptide comprises SEQ ID NO: 3 with a mutation at a position corresponding to proline 402 of SEQ ID NO: 3, a mutation at a position corresponding to proline 564 of SEQ ID NO: 3, and a mutation at a position corresponding to asparagine 803 of SEQ ID NO: 3.

8. The polynucleotide of claim 6, wherein the mutation at a position corresponding to proline 402 of SEQ ID NO: 3 is to alanine, the mutation at a position corresponding to proline 564 of SEQ ID NO: 3 is to glycine, or the mutation at a position corresponding to asparagine 803 of SEQ ID NO: 3 is to alanine.

9. The polynucleotide of claim 3, wherein the polypeptide comprises the sequence as set forth in SEQ ID NO: 2.

10. The polynucleotide of claim 3, wherein the nucleotide sequence comprises the sequence as set forth in SEQ ID NO: 1.

11. A vector comprising the endothelial cell-specific promoter of claim 1.

12. A vector comprising the polynucleotide of claim 3.

13. The vector of claim 12, wherein the polypeptide comprises SEQ ID NO: 3 with a mutation at a position corresponding to proline 402 of SEQ ID NO: 3, a mutation at a position corresponding to proline 564 of SEQ ID NO: 3, or a mutation at a position corresponding to asparagine 803 of SEQ ID NO: 3.

14. The vector of claim 13, wherein the mutation at a position corresponding to proline 402 of SEQ ID NO: 3 is to alanine, the mutation at a position corresponding to proline 564 of SEQ ID NO: 3 is to glycine, or the mutation at a position corresponding to asparagine 803 of SEQ ID NO: 3 is to alanine.

15. The vector of claim 11, wherein the vector is an adenovirus vector.

16. The vector of claim 12, wherein the vector is an adenovirus vector.

17. The vector of claim 15, wherein the adenovirus vector is adenovirus serotype 5 vector.

18. The vector of claim 16, wherein the adenovirus vector is adenovirus serotype 5 vector.

19. A pharmaceutical composition comprising the vector of claim 15 and a pharmaceutically acceptable carrier.

20. A pharmaceutical composition comprising the vector of claim 16 and a pharmaceutically acceptable carrier.

21. A vector comprising the polynucleotide of claim 9.

22. The vector of claim 21, wherein the vector is an adenovirus vector.

23. The vector of claim 22, wherein the adenovirus vector is adenovirus serotype 5 vector.

* * * * *